US012508414B2

(12) United States Patent
Albertsen et al.

(10) Patent No.: US 12,508,414 B2
(45) Date of Patent: Dec. 30, 2025

(54) SINGLE USE SAFETY CAP FOR USE WITH NEEDLELESS CONNECTORS

(71) Applicant: Quest Medical, Inc., Allen, TX (US)

(72) Inventors: Jeffrey Albertsen, McKinney, TX (US); Robert Mart, Colleyville, TX (US); Andrew Nelson, Dallas, TX (US); Savan Patel, Plano, TX (US)

(73) Assignee: Quest Medical, Inc., Allen, TX (US)

( * ) Notice: Subject to any disclaimer, the term of this patent is extended or adjusted under 35 U.S.C. 154(b) by 866 days.

(21) Appl. No.: 17/579,494

(22) Filed: Jan. 19, 2022

(65) Prior Publication Data

US 2023/0226338 A1 Jul. 20, 2023

(51) Int. Cl.
*A61M 39/20* (2006.01)
*A61M 39/10* (2006.01)

(52) U.S. Cl.
CPC ........ *A61M 39/20* (2013.01); *A61M 39/1011* (2013.01); *A61M 2039/1033* (2013.01)

(58) Field of Classification Search
CPC .. A61M 39/10; A61M 39/20; A61M 39/1011; A61M 2039/1033; A61M 2039/1044; A61M 2039/1066; A61M 2039/1083; A61M 2039/1088; A61M 2039/1105; A61M 2039/1027; B65D 1/0246; B65D 41/3428; B65D 41/3442; B65D 41/3447; B65D 41/10; B65D 41/02; B65D 41/04; B65D 41/0478; B65D 41/0464; B65D 41/34; B65D 41/40; B65D 47/2087; B65D 50/041; B65D 49/12; B65D 2543/00333; A61J 1/1412; A61J 1/1418; A61J 1/1475
See application file for complete search history.

(56) References Cited

U.S. PATENT DOCUMENTS 6,095,353 A * 8/2000 Gargiulo .............. B65D 50/041 215/277
10,124,117 B2 * 11/2018 Wei ......................... A61M 5/24
2005/0201086 A1 * 9/2005 Friedrich ................ F16P 3/144 362/217.13
2011/0130025 A1 * 6/2011 Palinkas .............. H02G 15/013 29/857
2018/0256883 A1 * 9/2018 Follman .............. A61M 39/162
2021/0322749 A1 * 10/2021 Rothenberg ...... A61M 39/0247

* cited by examiner

*Primary Examiner* — Michael J Tsai
*Assistant Examiner* — Katerina A. Wittliff
(74) *Attorney, Agent, or Firm* — Stephen Y. Liu; Carstens, Allen & Gourley, LLP

(57) ABSTRACT

A safety cap for use with a needleless connector. The safety cap includes a body configured to at least partially enclose a head of the needleless connector (NC). The body is configured to achieve a first configuration that can be securely sealed to the NC and a second configuration that cannot be securely sealed to the NC. The second configuration is different from the first configuration. The safety cap also includes a detent in communication with the body which is configured to prevent the body from transitioning from the second configuration back to the first configuration.

8 Claims, 18 Drawing Sheets

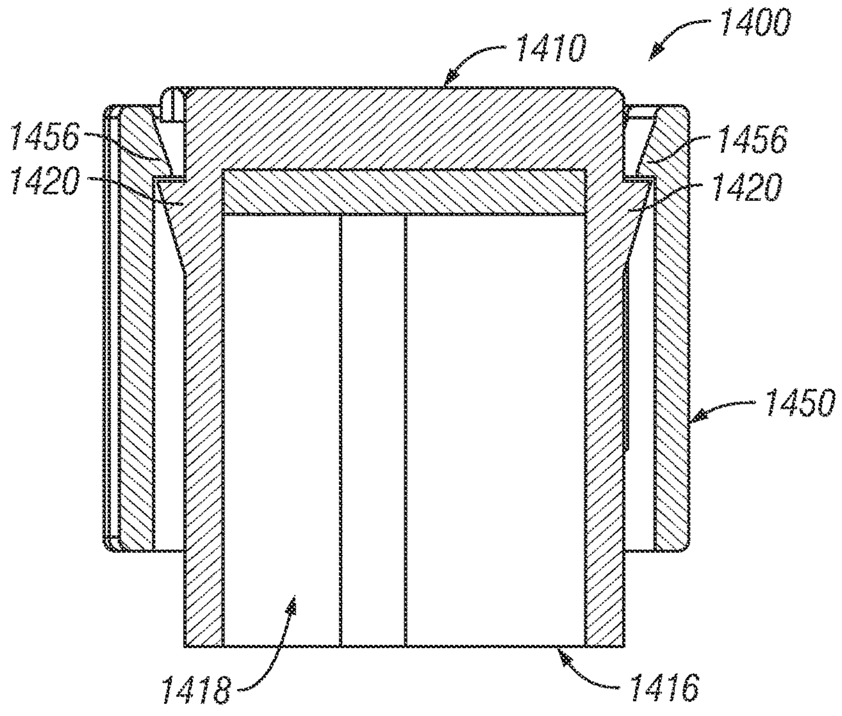
FIG. 18
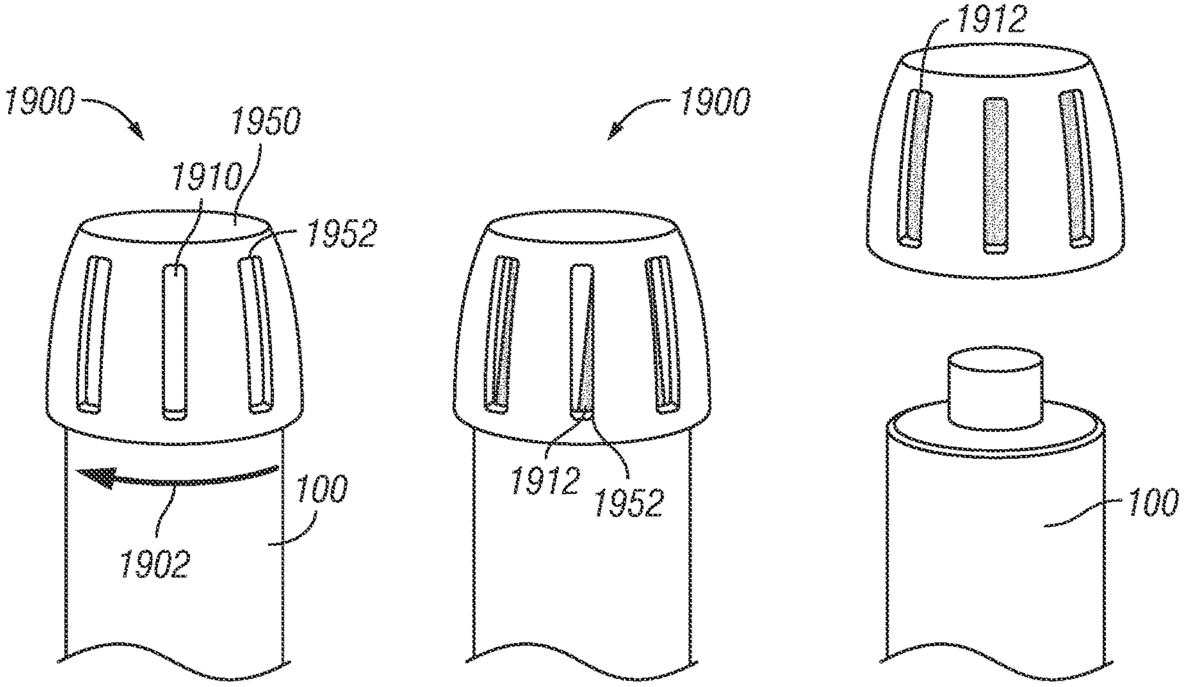
FIG. 19A
FIG. 19B
FIG. 19C

SINGLE USE SAFETY CAP FOR USE WITH NEEDLELESS CONNECTORS

BACKGROUND

Technical Field

The present disclosure relates to medical devices. More particularly, and not by way of limitation, the present disclosure is directed to a single use safety cap for needleless connectors and a corresponding method of use.

Description of Related Art

Needleless connectors (NCs) are transitional interfaces that permit the exchange of fluids between containers, fluid transfer devices, and/or fluid conduits. NCs were designed primarily for use in the medical field to prevent needlestick injuries to medical care professionals. The NCs are typically attached to the ends of vascular catheters or other tubular structures, such as branched intravenous (IV) lines, to facilitate access for infusion and aspiration without the need for needles.

NCs generally have a housing that define a fluid pathway between a distal end to a proximal end. For some NCs, the proximal end is configured to engage with a fluid distribution line, such as a catheter or IV, and the distal end is exposed to the environment and configured to engage with fluid transfer device, such as a syringe, or fluid sources, such as a vial. For other NCs, the proximal end is configured to engage with a fluid source, such as a vial, and the distal end is exposed to the environment and configured to engage with a fluid transfer device. The fluid pathway, which extends axially through the NC, is typically sealed by a movable septum at the distal end to prevent entry of pathogens or contaminants into the NC. The pathogens or contaminants could then proceed into the fluid distribution line before entering into the patient's body, causing infection. Alternatively, the pathogens or contaminants could proceed into the fluid source, which would result in contamination. Disinfection of the septum before attaching the fluid source to the NC is crucial for reducing the rate of preventable infections in medical care facilities.

BRIEF SUMMARY

Novel aspects of the present disclosure are directed to a safety cap for use with a needleless connector. The safety cap includes a body configured to at least partially enclose a head of the needleless connector (NC). The body is configured to achieve a first configuration that can be securely sealed to the NC and a second configuration that cannot be securely sealed to the NC. The second configuration is different from the first configuration. The safety cap also includes a detent in communication with the body. The detent is configured to prevent the body from transitioning from the second configuration back to the first configuration.

Novel aspects of the present disclosure are also directed to a system for introducing fluids to a patient. The system includes a tube configured to provide intravenous fluids to the patient. A proximal end of the tube interfaces with a blood vessel of the patient and a needleless connector (NC) is attached to a distal end of the tube. A safety cap is connected to the needleless connector. The safety cap includes a body configured to at least partially enclose a head of the needleless connector (NC). The body is configured to achieve a first configuration that can be securely sealed to the NC and a second configuration that cannot be securely sealed to the NC. The second configuration is different from the first configuration. The safety cap also includes a detent in communication with the body. The detent is configured to prevent the body from transitioning from the second configuration back to the first configuration.

Other aspects, embodiments and features of the invention will become apparent from the following detailed description of the invention when considered in conjunction with the accompanying figures. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

FIG. 18 is a cross sectional view of the other safety cap according to an illustrative embodiment;

FIG. 19A-19C are various perspective views of a safety cap with a use indicator according to an illustrative embodiment;

DETAILED DESCRIPTION

Needleless connectors have been identified as a cause of catheter-related bloodstream infection (CRBSI). Inadequate disinfection of NCs allows pathogens to enter a patient's bloodstream, resulting in an expensive and time-consuming road to recovery. The average costs for treating CBRSI is about $48,000, with an increase in the length of stay (LoS) at the hospital by about 7 days. Patients suffering from CBRSI are 5 times more likely to be readmitted to the hospital and experience a 25% increase in mortality rate.

To combat CBRSI, specific disinfection guidelines have been implemented. For example, the current guidelines for engaging needleless connectors (NCs) are as follows: for every engagement, scrub the surface of the NC with an alcohol wipe for 30 seconds, allow the NC to dry for 20 seconds, and then cap the NC when not engaged. In another example, the current guidelines for intravenous (IV) line access with a regular cap are as follows: remove cap, disinfect the exposed surfaces of the needleless connector, connect syringe with saline to check patency, disconnect the syringe, clean the needleless connector again, connect syringe or IV set with medication and deliver, disconnect the syringe or IV, clean the needleless connector again, connect syringe with saline to flush, and disconnect and place a new cap on the needleless connector.

These current disinfection guidelines are complex. Compliance with these guidelines can vary due to subjective interpretation of the steps and due to events occurring within specific medical settings. For example, the manual disinfection with the alcohol wipe can include multiple steps over multiple interfaces. Time requirements are sometimes not followed. Additionally, single-use caps are sometimes reused, particularly when replacement caps are not available. Sometimes, caps are improperly attached or not used at all. Even conventional, single-use disinfection caps that purport to eliminate the need to disinfect the NC prior to use suffer from user error. For example, some medical care providers continue to disinfect the NC because they do not know if it was previously attached correctly or if it was removed and reused. Thus, novel aspects of the present disclosure recognize the need for a safety cap that self-modifies to prevent reuse to eliminate the uncertainty faced by medical care providers.

Figure 1:
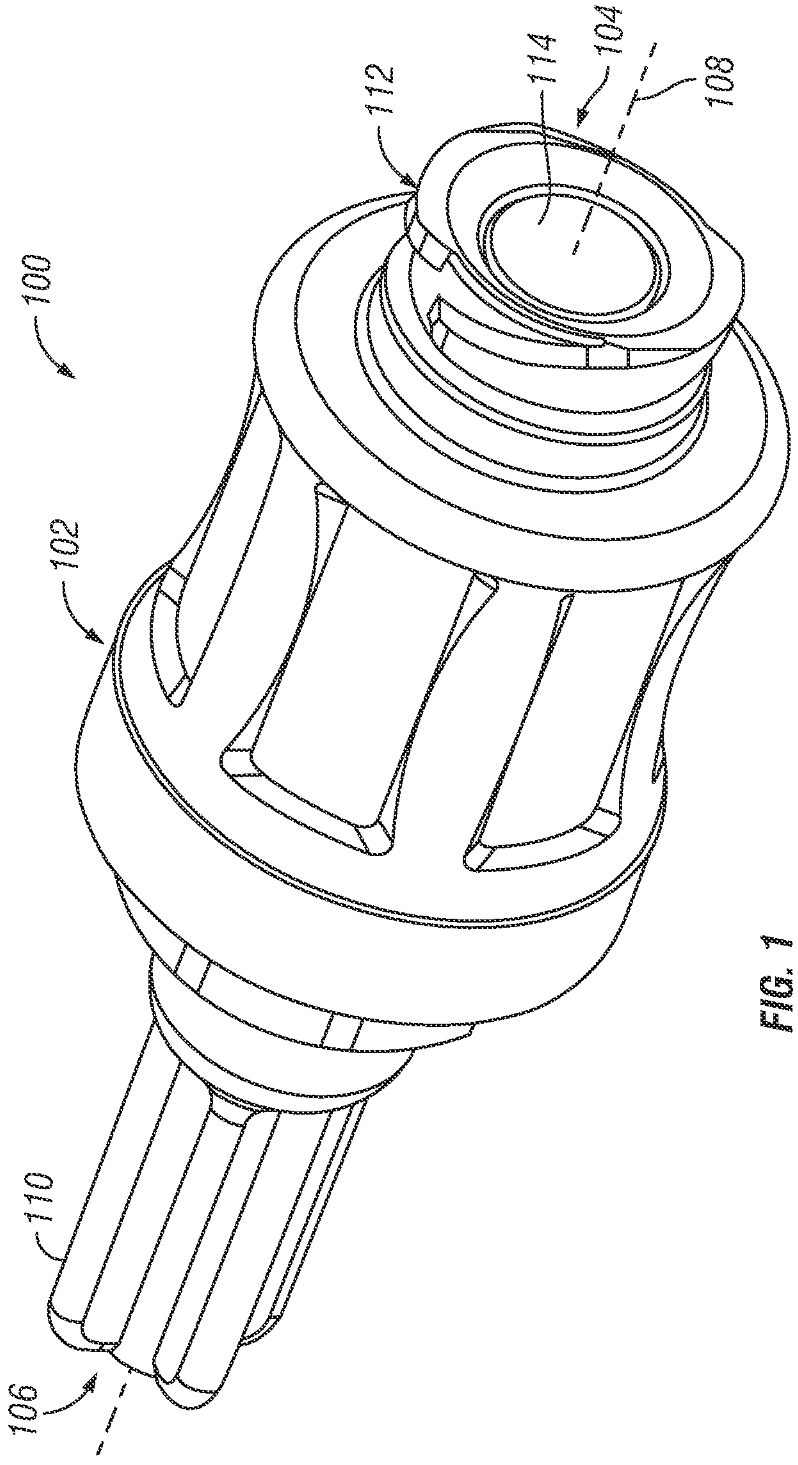
FIG. 1 is a perspective view of a needleless connector.

FIG. 1 is a perspective view of an exemplary needleless connector. When attached to a terminal end of a fluid conduit, such as an IV or catheter, the NC 100 selectively seals the fluid conduit to prevent ingress of pathogens and contaminants when not actively in use, but which can permit infusion or aspiration of fluids as required.

The NC 100 includes a housing 102 having a distal end 104 and a proximal end 106. The NC 100 defines a fluid pathway between the distal end 104 and the proximal end 106, coinciding with the axis 108. A tail 110 at the proximal end 106 is configured to engage with a tube (not shown). In this example in FIG. 1, the tail 110 is a narrow, elongated structure configured to be frictionally fit inside of a receiver, such as the terminal end of a tube. A head 112 projects outwardly from the housing 102 at the distal end 104 and is configured to be removably engaged with a receiving end of a fluid transfer device (not shown), such as a syringe, or a fluid dispenser, such as an IV bag or vial (also not shown). In this example in FIG. 1, a threaded interface is disposed on the exterior surface of the head 112 of the NC 100, which is configured to engage a threaded, interior sidewall of the fluid transfer device. In a non-limiting embodiment, the threaded interface of NC 100 is a luer lock fitting.

To prevent the ingress of pathogens into the attached tube via the NC 100, the fluid pathway can be sealed by a movable septum 114 that is partially exposed at distal end 104 of the NC. In one embodiment, the movable septum 114 is an exposed surface of a compressible valve housed within the housing 102. When the compressible valve is exposed to a compression force, the septum 114 disengages from the distal end 104 of the NC 100 to expose an opening that allows fluid to pass from a fluid dispenser through the NC 100 and into the attached tube. The compression force is generally applied to the septum 114 by attachment of a fluid transfer device or fluid source to the head 112 of the NC 100, causing the fluid transfer device or fluid source to engage with the septum 114, unsealing the septum 114 from the distal end 104 of the NC 100.

Figure 2:
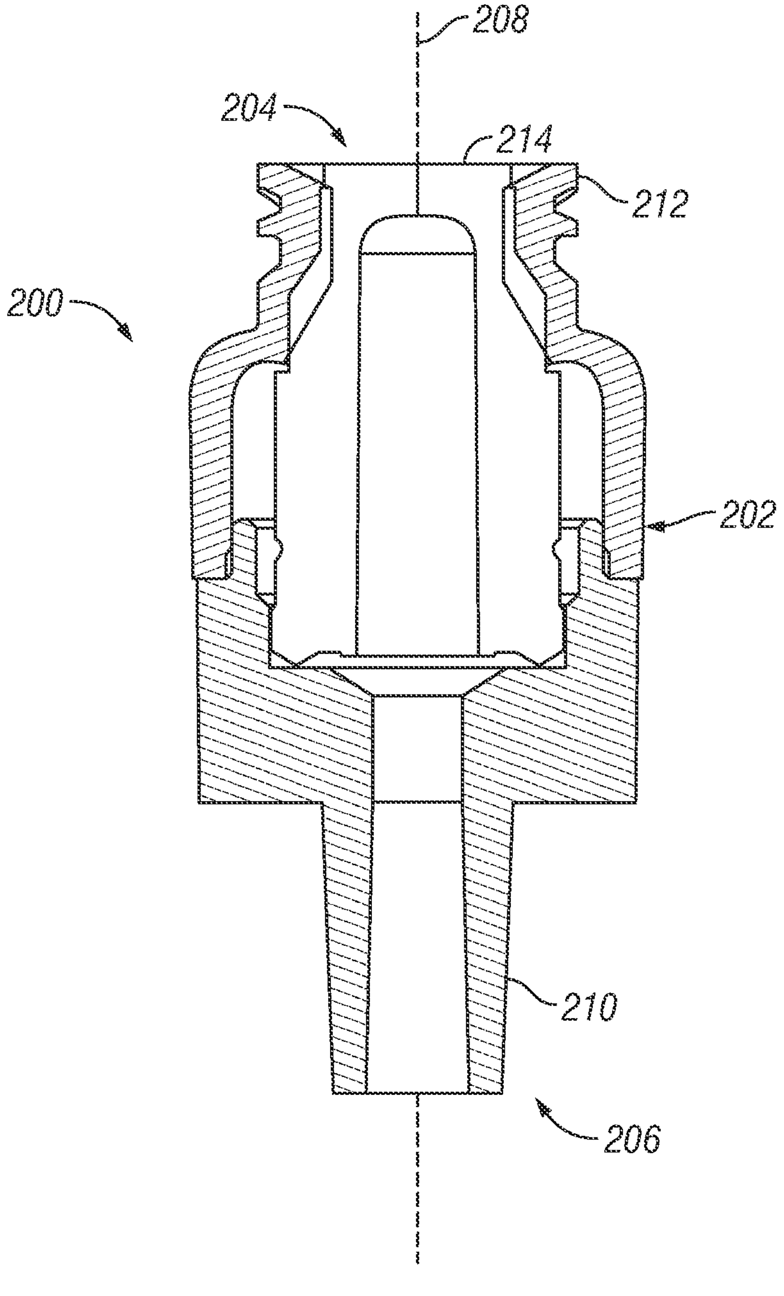
FIG. 2 is a partial cutaway side view of another exemplary needleless connector.

FIG. 2 is a partial cutaway side view of another exemplary needleless connector. The NC 200 is configured to attach to and selectively seal containers of liquid, e.g., vials, to prevent ingress of pathogens when not in use. The NC 200 can permit infusion or aspiration of fluids as required.

The NC 200 includes a housing 202 having a distal end 204 and a proximal end 206. The NC 200 defines a fluid pathway between the distal end 204 and the proximal end 206, coinciding with the axis 208. A tail 210 is concealed within the housing 202 and accessible from the proximal end 206 of the NC 200. The tail 210 is configured to be inserted into a container (not shown). In some embodiments, the tail is a narrow, elongated structure with a tapered point that is configured to puncture container seals. A head 212 projects outwardly from the housing 202 at the distal end 204 and is configured to be removably engaged with a receiving end of a fluid transfer device (not shown), such as a syringe. In this example in FIG. 2, a threaded interface is disposed on the exterior surface of the head 212 of the NC 200, which is configured to engage a threaded, interior sidewall of the fluid transfer device. In a non-limiting embodiment, the threaded interface of NC 200 is a luer lock fitting.

To prevent the ingress of pathogens into the attached tube via the NC 200, the fluid pathway can be sealed by a movable septum 214 that is partially exposed at distal end 204 of the NC. In one embodiment, the movable septum 214 is an exposed surface of a compressible valve housed within the housing 202. When the compressible valve is exposed to a compression force, the septum 214 disengages from the distal end 204 of the NC 200 to expose an opening that allows fluid to pass from a fluid dispenser through the NC 200 and into the attached tube. The compression force is generally applied to the septum 214 by attachment of a fluid transfer device to the head 212 of the NC 200, causing the fluid transfer device or fluid source to engage with the septum 214, unsealing the septum 214 from the distal end 204 of the NC 200.

Figure 3:
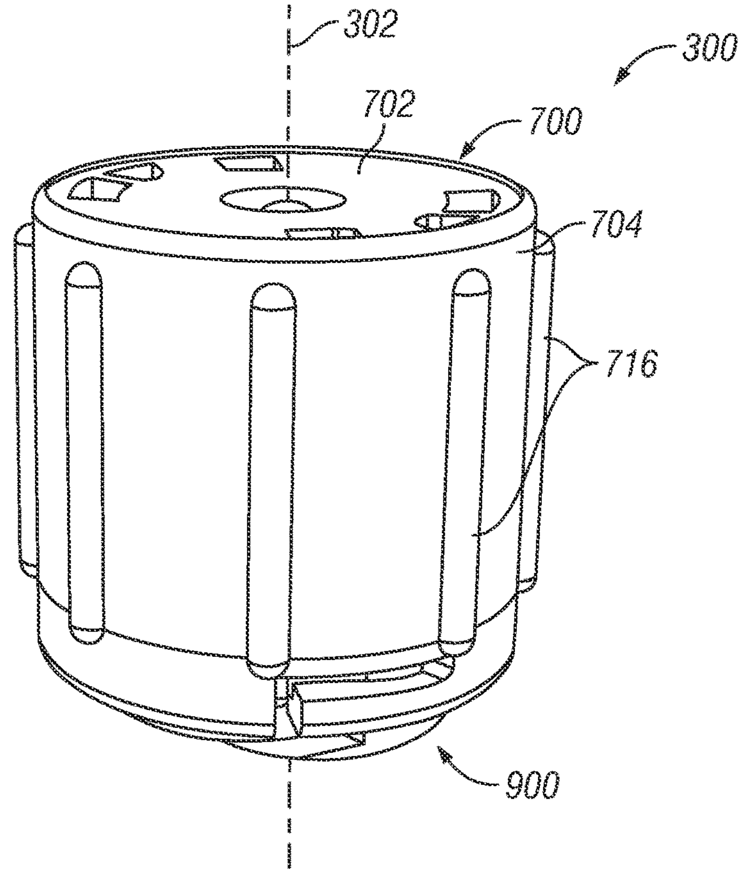
FIG. 3 is a perspective view of a safety cap in an unused configuration according to an illustrative embodiment.
Figure 4:
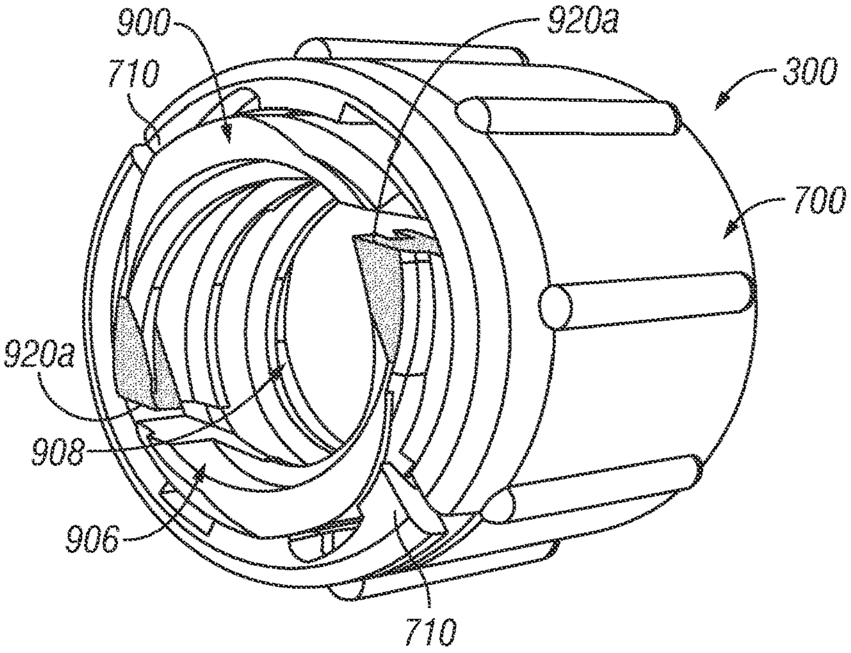
FIG. 4 is another perspective view of the safety cap an unused configuration according to an illustrative embodiment.

FIGS. 3 and 4 are various perspective views of a safety cap in an unused configuration according to an illustrative embodiment. The safety cap 300 can be coupled to an NC, such as NC 100 in FIG. 1, to seal an opening at the distal end of the NC. In this embodiment in FIG. 3, the safety cap 300 is generally cylindrical with an end wall 702 at a first end which is separated from an opening 906, shown in FIG. 4, at a second end by a side wall 704. The opening 906 at the second end is sized to receive a head of a conventional NC.

The safety cap 300 is formed from a first cap portion 900, which may be referred to in the alternative as an inner cap 900, and a second cap portion 700, which may be referred to in the alternative as an outer cap 700. The inner cap 900 is housed within a cavity of the outer cap 700 and aligned coaxially to the outer cap 700. Axis 302 is an axis common to both the inner cap 900 and the outer cap 700. Additionally, the inner cap 900 is rotatably engaged with the outer cap 700 to allow the inner cap 900 and the outer cap 700 to rotate relative to one another, at least until the inner cap and the outer cap lock together by mating of a track follower and a receiving groove, as described in more detail in FIG. 11 that follows.

In the unused configuration, the inner cap 900 extends out of the second end of the outer cap 700. The rotation of the inner cap 900 and the outer cap 700 to secure the safety cap 300 onto an NC causes the inner cap 900 to advance into the cavity of the outer cap 700 until their respective second ends are substantially flush, as can be seen in the used configuration depicted in FIGS. 5 and 6. In the used configuration, the inner cap 900 and the outer cap 700 are locked together to prevent the safety cap 300 from reassuming the unused configuration.

A set of elongated ridges 716 are disposed regularly around an exterior surface of the side wall 704 to provide a textured surface that can be more easily engaged by a user. As used herein, the term “set” means one or more. Thus, the set of elongated ridges can be a single elongated ridge or two or more elongated ridges. In this illustrative embodiment, the set of elongated ridges 716 includes a plurality of ridges disposed regularly around the circumference of the outer cap 700. In other embodiments, the set of elongated ridges 716 can be replaced by other grip-enhancing features.

In this illustrative embodiment, the safety cap 300 changes configuration during operation to prevent reattachment to an NC. The safety cap 300 can change its configuration as the safety cap 300 is attached to an NC, or as the safety cap 300 is removed from the NC. In this illustrative embodiment, the safety cap 300 changes its configuration as the safety cap 300 is attached to an NC. Specifically, the rotational force exerted on the outer cap 700 causes the inner cap 900 to advance further into the cavity of the outer cap 700, causing the safety cap 300 to change from a first configuration to a second configuration. In the second configuration, the safety cap 300 cannot be reattached to an NC. Further, the safety cap 300 can be locked into the second configuration to prevent the safety cap 300 from being reused.

FIG. 4 is another perspective view of the safety cap in FIG. 3 in an unused configuration according to an illustrative embodiment. The view depicted in FIG. 4 is from the second end, looking into a cavity 908 of the inner cap 900, which is configured to receive a head of an NC. The inner cap 900 includes engagement interface 920 formed from a leading edge **920*a* and a deformable thread portion 920*b***. In this illustrative environment the attachment interface is a threaded interface, such as can be found in a luer lock interface.

As can be seen from FIGS. 3 and 4, in the unused configuration the inner cap 900 extends outside of the outer cap 700 from the second end. Additionally, the set of thread deformers 710 are offset from the set of deformable thread portions **920*b*, which can also be seen in more detail in the alternate view in FIG. 13. As the safety cap 300 is coupled to an NC, the inner cap 900 advances further into the cavity 708 of the outer cap 700. At the same time, the inner cap 900 and the outer cap 700 rotate relative to one another, causing the set of thread deformers 712 of the outer cap 700 to engage with the set of deformable thread portions 920*b* of the inner cap 900, which prevents the safety cap 300** from being reattached to another NC.

Figure 5:
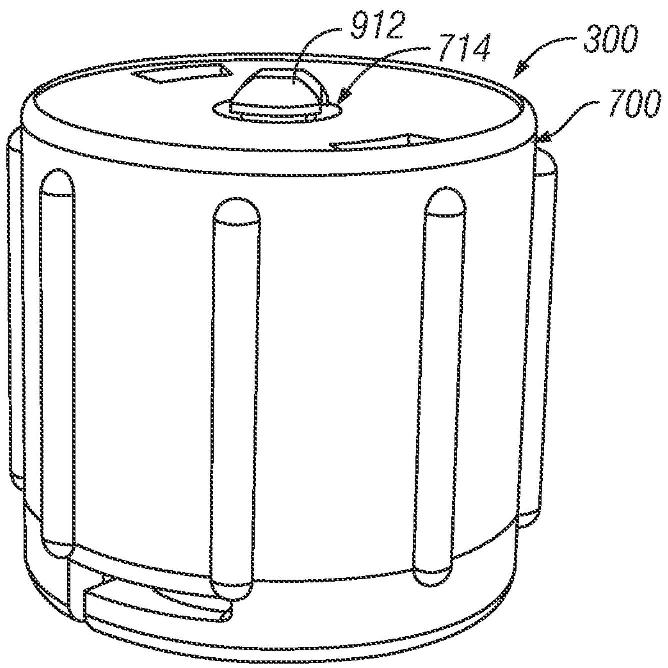
FIG. 5 is a perspective view of the safety cap in used configuration according to an illustrative embodiment.
Figure 6:
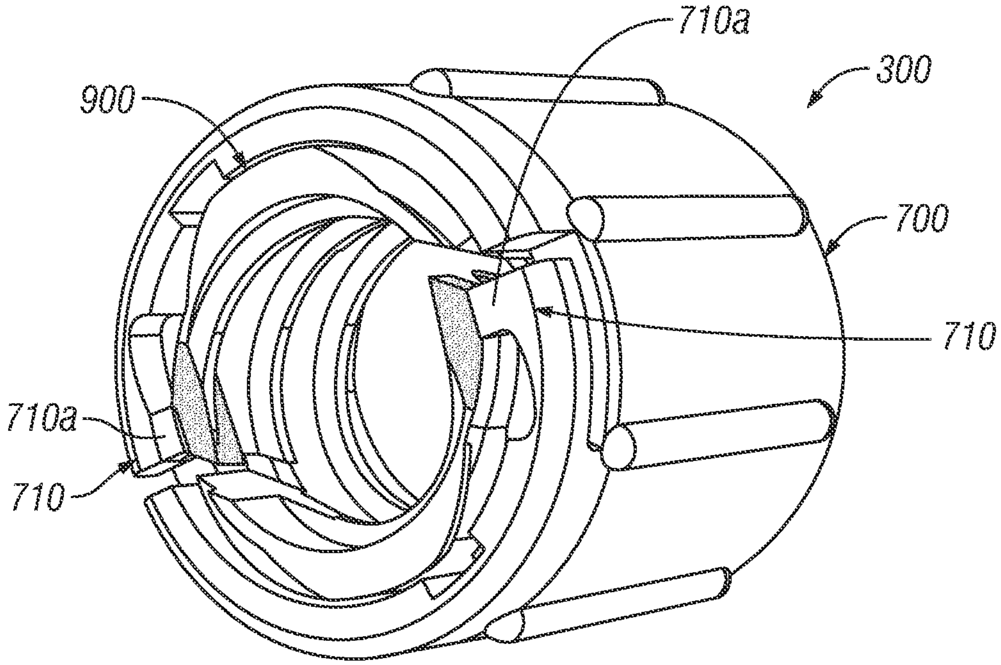
FIG. 6 is another perspective view of the safety cap in a used configuration according to an illustrative embodiment.

FIGS. 5 and 6 are various perspective views of the safety cap in FIG. 3 in a used configuration according to an illustrative embodiment. In the used configuration, the inner cap 900 is generally recessed entirely within the cavity 708 of the outer cap 700. The safety cap 300 can be locked into this used configuration to prevent the safety cap from reassuming the unused configuration. In a non-limiting embodiment, the safety cap 300 can be locked into this configuration when the locking cap 912 projecting outwardly from the inner cap 900 is forced through the locking aperture 714 passing through the end wall 702 of the outer cap 700.

With particular reference to FIG. 6, in the used configuration the set of thread deformers 710 are shown in contact with the set of deformable thread portions **920*b*. Contact between the set of thread deformers 710 and the set of deformable thread portions 920*b* causes the safety cap 300 to self-deform, which prevents the safety cap 300 from reattaching to an NC. In this embodiment, self-deformation of the safety cap 300 is caused by a force applied to the set of deformable thread portions 920*b* by the set of thread deformers 710. As described in more detail in FIG. 10, the self-deformation of the inner cap 900 can occur by changing a thread pitch at a leading edge 920*a* of the engagement interface 920, or by changing an effective diameter of the opening 906. In either embodiment, the self-deformation prevents the safety cap 300** from reattaching to an NC.

Figure 10:
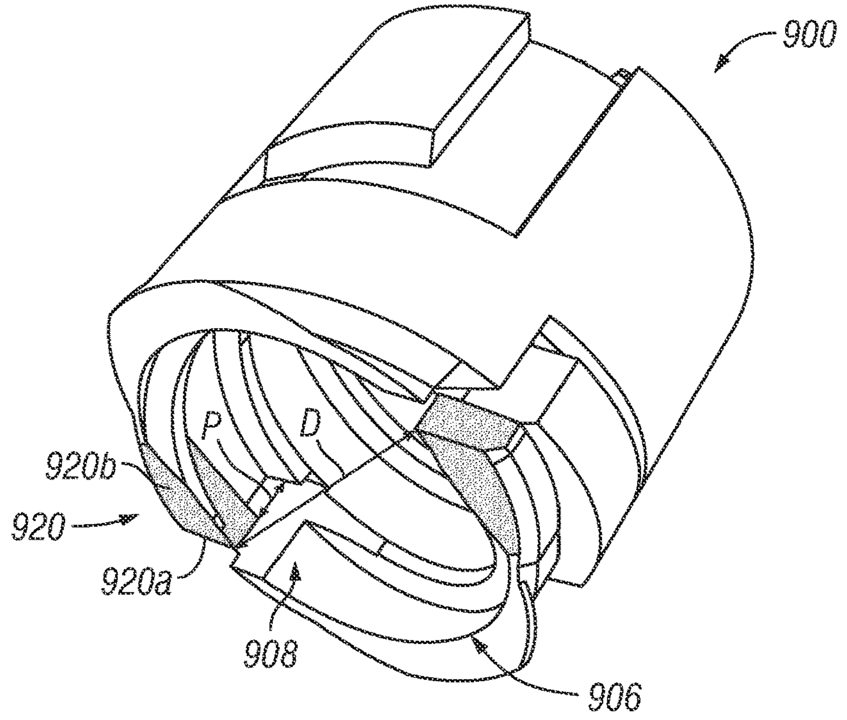
FIG. 10 is another perspective view of the inner cap of the safety cap according to an illustrative embodiment.

The location of engagement between each of the ledges **710*a* of the set of thread deformers 710 with a respective one of the set of deformable thread portions 920*b* determines how the safety cap 300 self-deforms. In the illustrative embodiment shown in FIG. 6, the ledges 710*a* engage the set of deformable thread portions 920*b* on surfaces that are co-planar with an imaginary plane that is normal to the axis 302. Accordingly, the set of thread deformers 710 changes a thread pitch of the engagement interface 920 disposed on the interior surface of sidewall 904 of the inner cap 900. In the embodiment in which each of the ledges 710*a* of the set of thread deformers 710 engages with the deformable thread portions 920*b* that coincide with the curved, external surface of the side wall 904, then the self-deformation results in a decrease in the effective diameter of the inner cap 900. The effective diameter of the inner cap 900 is shown in FIG. 10**.

Figure 7:
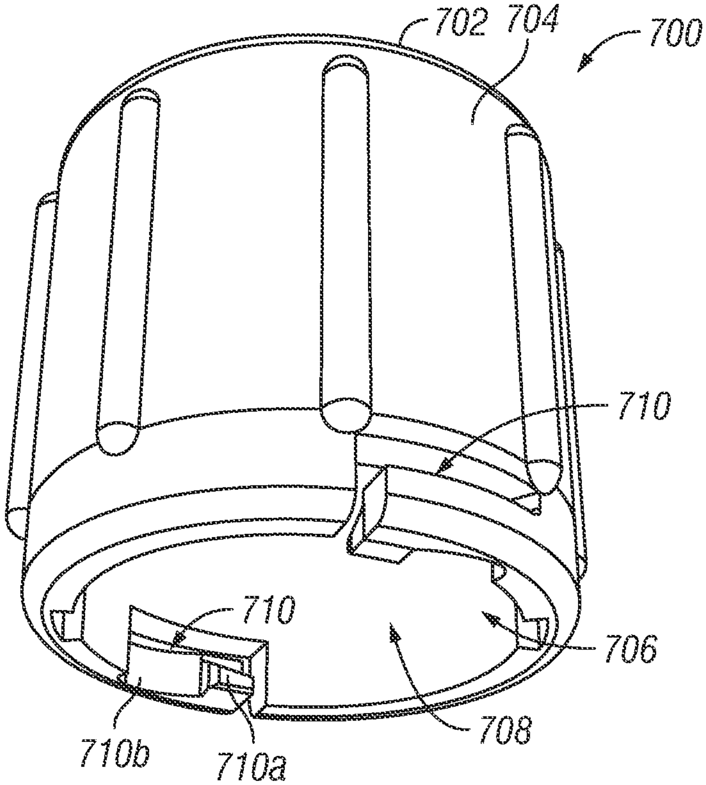
FIG. 7 is a perspective view of the outer cap of the safety cap according to an illustrative embodiment.
Figure 8:
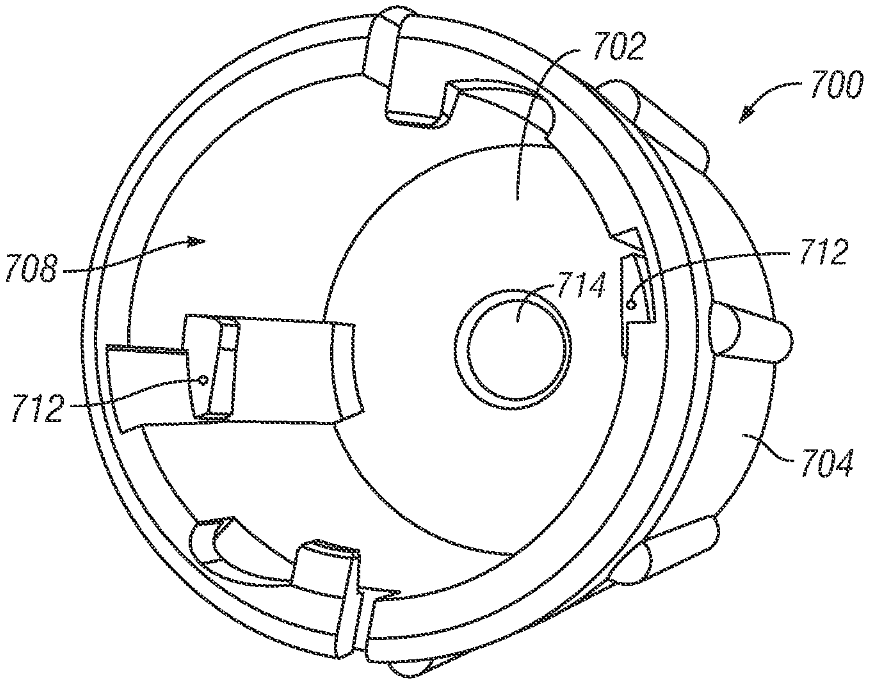
FIG. 8 is another perspective view of the outer cap of the safety cap according to an illustrative embodiment.

FIGS. 7 and 8 are perspective views of the outer cap of the safety cap according to an illustrative embodiment. In particular, FIG. 7 provides a more detailed view of the set of thread deformers located at the second end of the outer cap 700 and FIG. 8 provides a more detailed view of the set of track followers disposed on the interior surface of the side wall.

The outer cap 700 is generally cylindrical with an end wall 702 at a first end which transitions into a side wall 704. The outer cap 700 also has an opening 706 at a second end that is opposite to the first end. The outer cap 700 defines a cavity 708 that is sized to receive an inner cap 900 that is shown in more detail in FIG. 9.

With particular reference to FIG. 7, the set of thread deformers 710 depicted is integrally formed into the lip of the side wall 704 that defines the opening 706. However, in other embodiments, the set of thread deformers 710 can be removably or fixedly attached to the side wall 704 using conventional means, such as adhesives or fasteners. One example of a removably attached set of thread deformers is shown in FIGS. 24A-24C.

Each of the set of thread deformers 710 has a ledge 710*a* projecting radially inward, which reduces an effective radius of the outer cap 700. Also, each ledge 710*a* is disposed at the end of a flexing hinge 710*b* that allows the corresponding ledge 710*a* to deflect radially inward and radially outward. As described in more detail in the paragraphs that follow, the set of thread deformers 710 is configured to engage with and deform a set of deformable thread portions disposed on the inner cap 900, which can prevent reattachment of the safety cap onto an NC.

With particular reference to FIG. 8, a set of track followers 712 is disposed on an interior surface of the side wall 704, projecting radially inward. In this illustrative embodiment, the set of track followers 712 is formed from two track followers located on opposite sides of the outer cap 700. The set of track followers 712 are sized and positioned to be received by an alignment track disposed on an exterior surface of the side wall 904 of the inner cap 900, as shown in more detail in FIGS. 9 and 10 that follow.

A locking aperture 714 passing through the end wall 702 is sized to receive a locking post that locks the inner cap 900 and the outer cap 700 when the safety cap 300 is in the used configuration. Engagement of the locking post with the locking aperture 714 prevents the inner cap 900 from withdrawing back into a cavity 708 of the outer cap 700.

Figure 9:
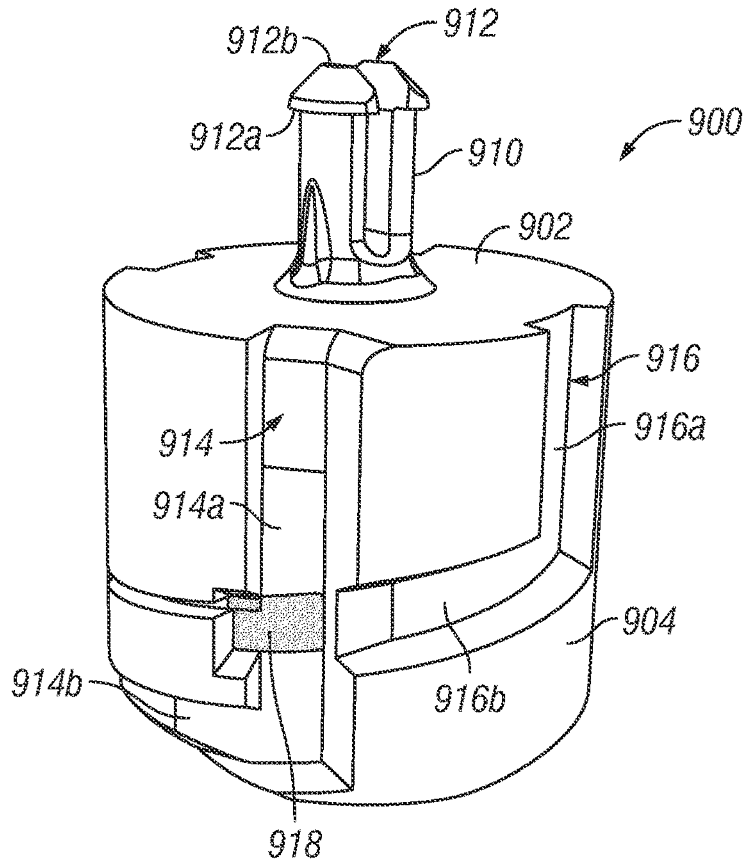
FIG. 9 is perspective view of the inner cap of the safety cap according to an illustrative embodiment.

FIGS. 9 and 10 are perspective views of the inner cap of the safety cap 300 according to an illustrative embodiment. In particular, FIG. 9 provides a more detailed view of a set of alignment tracks disposed on an exterior surface of the side wall 904 of the inner cap 900, and FIG. 10 provides a more detailed view of the set of deformable threads disposed at a second end of the outer cap 900.

The inner cap 900 is generally cylindrical with an end wall 902 at a first end which transitions into a side wall 904. The inner cap 900 also has an opening 906 at a second end that is opposite to the first end. The inner cap 900 defines a cavity 908 that is sized to receive a threaded head of an NC, such as head 112 of NC 100 in FIG. 1. In this illustrative embodiment, a locking post 910 extends normally from the end wall 902 and coincides with the axis 302 when coupled with the outer cap 700. The locking post 910 includes a frusto-conical locking cap 912 at the end with a base 912*a* that has a diameter that is larger than the diameter of the locking post 910. The shape of the cap 912 allows the tip 912*b* of the locking post 910 to advance through the aperture 714 in the end wall 702 of the outer cap 700 but prevents the cap 912 from withdrawing back through the aperture 714 in the end wall 702. In the depicted embodiment, the locking post 910 is bifurcated into two halves which allows the cap 912 to deflect towards each other to reduce its effective diameter as it is being passed through the aperture 714.

The inner cap 900 includes a first set of guidance channels 914 configured to receive the set of thread deformers 710 of the outer cap 700. The first set of guidance channels 914 has a first segment 914*a* oriented parallel to the axis 302 and a second segment 914*b* that extends circumferentially (at least partially) around the inner cap 900. To assemble the safety cap 300, the set of thread deformers 710 of the outer cap 700 is aligned with the first segment 914*a* of the set of guidance channels 914, and then the inner cap 900 is advanced into the cavity 708 of the outer cap 700 until the set of thread deformers 710 reaches an end of the first segment 914*a* of the first set of guidance channels 914. When the safety cap 300 is attached to an NC, a rotational force exerted on the outer cap 700 causes the set of thread deformers 710 to advance through the second segment 914*b* until the set of thread deformers 710 engages with the set of deformable thread portions 920*b* located at an end of the first set of guidance channels 914. The set of deformable thread portions 920*b* is depicted in more detail in FIG. 10 and described with more particularity in the paragraphs that follow.

The inner cap 900 also includes a second set of guidance channels 916 configured to receive the set of track followers 712 disposed on an interior surface of the side wall 704 of the outer cap 700. The second set of guidance channels 916 includes a first segment 916*a* oriented parallel to the axis 302 and a second segment 916*b* that extends circumferentially (at least partially) around the inner cap 900. To assemble the safety cap 300, the set of track followers 712 are aligned with the first segment 916*a* of the second set of guidance channels 916 and the inner cap 900 is advanced into the cavity 708 of the outer cap 800 until the set of track followers 712 reaches an end of the first segment 916*a* of the second set of guidance channels 916. When the safety cap 300 is attached to an NC, a rotational force exerted on the outer cap 700 causes the set of track followers 712 to advance through the second segment 916*b* until the set of track followers 712 arrives at the end of the second set of guidance channels 916.

At the end of at least one of the set of second segments 916*b* of the second set of guidance channels 916 is a receiving groove 918 configured to mate with one of the set of track followers 712 to prevent the outer cap 700 and the inner cap 900 from rotating independently of one another. In this illustrative embodiment, the receiving groove(s) 918 is formed at an intersection of the first set of guidance channels 914 and the second set of guidance channels 916. In a non-limiting embodiment, when one of the set of track followers 712 reaches a corresponding receiving groove 918, the set of thread deformers 710 also reaches a corresponding one of the set of deformable thread portions 920*b*.

With reference to FIG. 10, the inner cap 900 is shown from the second end, looking into the cavity 908. An engagement interface 920 is disposed on an interior surface of the side wall 704, which is configured to engage with a corresponding engagement surface disposed on an exterior surface of the head of an NC. In an illustrative embodiment, the engagement interface 920 is a luer lock interface. The engagement interface 920 includes leading edges 920*a* and deformable thread portions 920*b*, which operate as previously described. The deformable thread portions 920*b* are features that can deform upon application of a force imparted upon the deformable thread portions 920*b* by a corresponding one of the set of thread deformers 710. The deformation of the deformable thread portions 920*b* prevents the safety cap 300 from being reattached to an NC after removal.

In one non-limiting embodiment, engagement of the set of thread deformers 710 with the set of deformable thread portions **920*b* imparts a force to the set of deformable thread portions 920*b* in the axial direction which reduces a thread pitch P between the leading edge 920*a* and the adjacent thread. The reduction of thread pitch P prevents the engagement interface 920 from engaging with the engagement interface of the NC, i.e., the luer lock disposed around the head of the NC. In another non-limiting embodiment, engagement of the set of thread deformers 710 with the set of deformable thread portions 920*b* imparts a force in the radial direction which reduces an effective diameter D of the opening 906 of the inner cap 900 of the safety cap 300. Reduction in the size of the opening 906 prevents insertion of the head of an NC into the corresponding cavity 908, which in turn prevents the safety cap 300** from being attached to the NC.

With reference to safety cap 300 described in FIGS. 3-13, the locking cap 912, the thread deformers 710, and the engagement interface 920 form a detent. Broadly defined, a detent is a feature formed from one or more elements which prevents a safety cap from reassuming the unused configuration after the safety cap has already assumed the used configuration. A coupling force received by the safety cap 300 causes the set of thread deformers 710 to engage with the engagement interface 920 to prevent the safety cap 300 from being reattached to the head of another NC. The locking cap 912 prevents the set of thread deformers 710 from disengaging from the engagement interface 920, which prevents the safety cap 300 from changing from the used configuration, shown in FIGS. 5 and 6, back into the unused configuration, shown in FIGS. 3 and 4.

Figure 11:
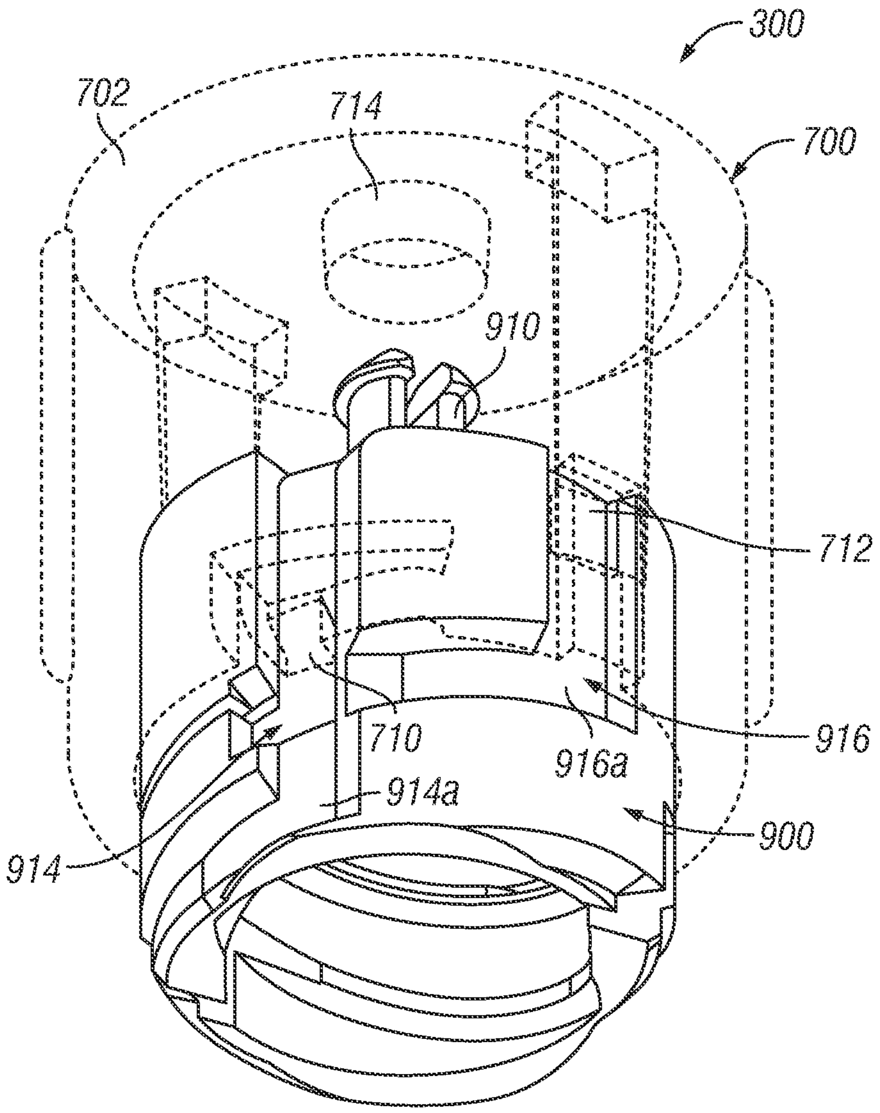
FIG. 11 is a perspective view of the safety cap in a partially assembled configuration according to an illustrative embodiment.

FIG. 11 is a perspective view of the safety cap in a partially assembled configuration according to an illustrative embodiment. Assembly of the safety cap 300 begins by aligning the set of thread deformers 710 with the first set of guidance channels 914. At the same time, the locking post 910 of the inner cap 900 is also aligned with the locking aperture 714 in the end wall 702 of the outer cap 700. The set of track followers 712 is also aligned with the second set of guidance channels 916 at the same time. The inner cap 900 is advanced into the cavity 708 of the outer cap 700 until the set of thread deformers 710 reaches an end of the first segment **914*a* of the first set of guidance channels 914 and until the set of track followers 712 reaches an end of the first segment 916*a* of the second set of guidance channels 916. In FIG. 11, the set of thread deformers 710 is about midway through the first segment 914*a* of the first set of guidance channels 914**.

Figure 12:
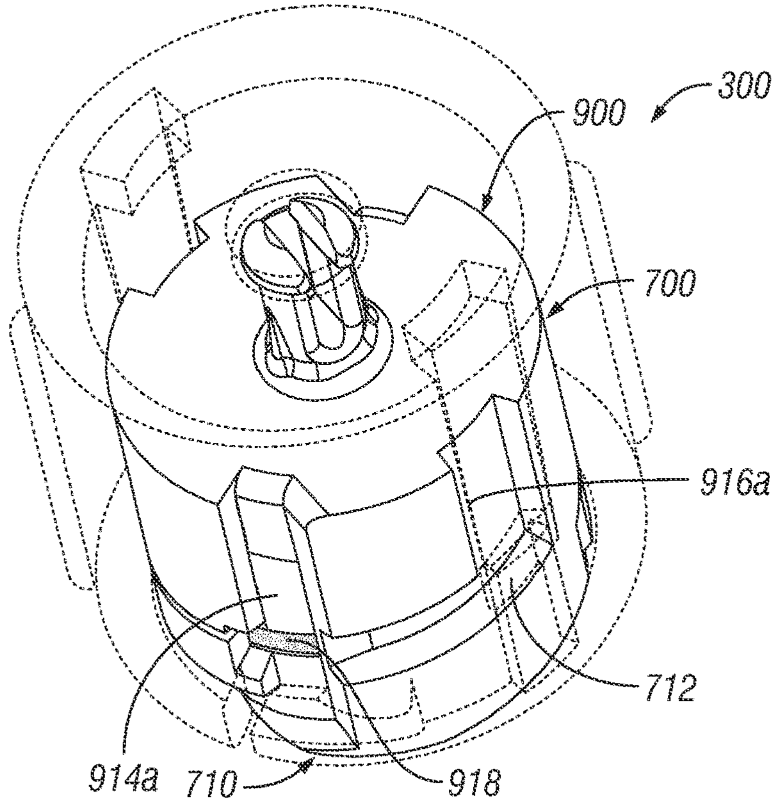
FIG. 12 is another perspective view of the safety cap in the unused configuration according to an illustrative embodiment.
Figure 13:
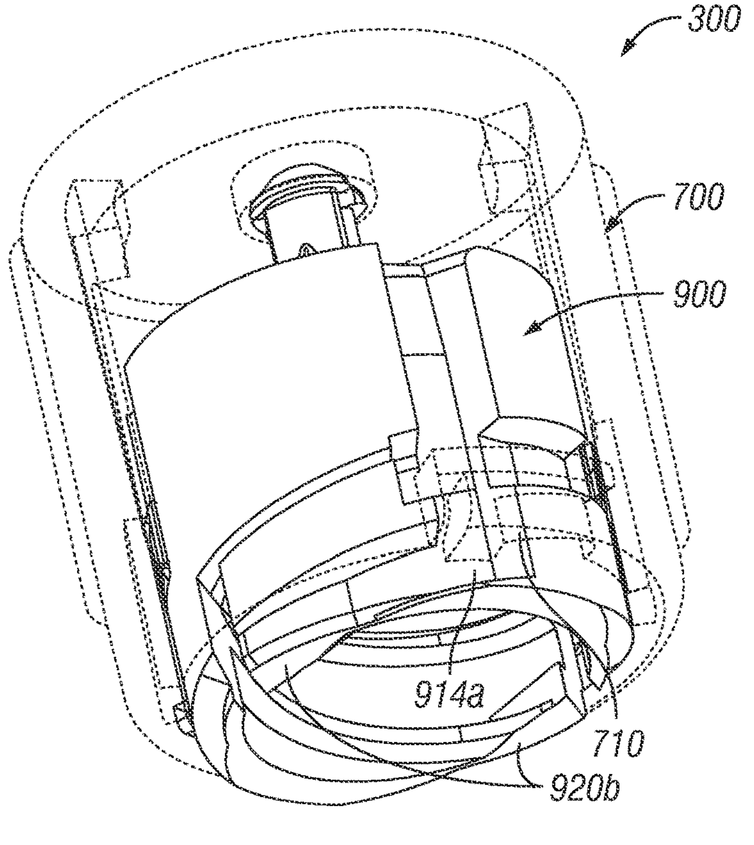
FIG. 13 is yet another perspective view of the safety cap in the unused configuration according to an illustrative embodiment.

FIGS. 12 and 13 are other perspective views of the safety cap in the unused state according to an illustrative embodiment. In particular, the set of thread deformers 710 are located at an end of the first segment **914*a* of the first set of guidance channels 914, and the set of track followers 712 are located at an end of the first segment 916*a* of the second set of guidance channels 916. A rotational force applied in the clockwise direction to the outer cap 700 causes the outer cap 700 and the inner cap 900 to rotate relative to one another until the set of track followers 712 mates with a corresponding one of the set of receiving grooves 918 and until the set of thread deformers 710 engages with a set of deformable thread portions 920*b*. When the inner cap 900 and the outer cap 700 are locked together, further clockwise rotation of the outer cap 700 causes tightening of the safety cap 300 onto the head of an NC. Counterclockwise rotation of the outer cap 700 causes loosening of the safety cap 300 from the head of the NC so that the safety cap 300** can eventually be removed.

Figure 14:
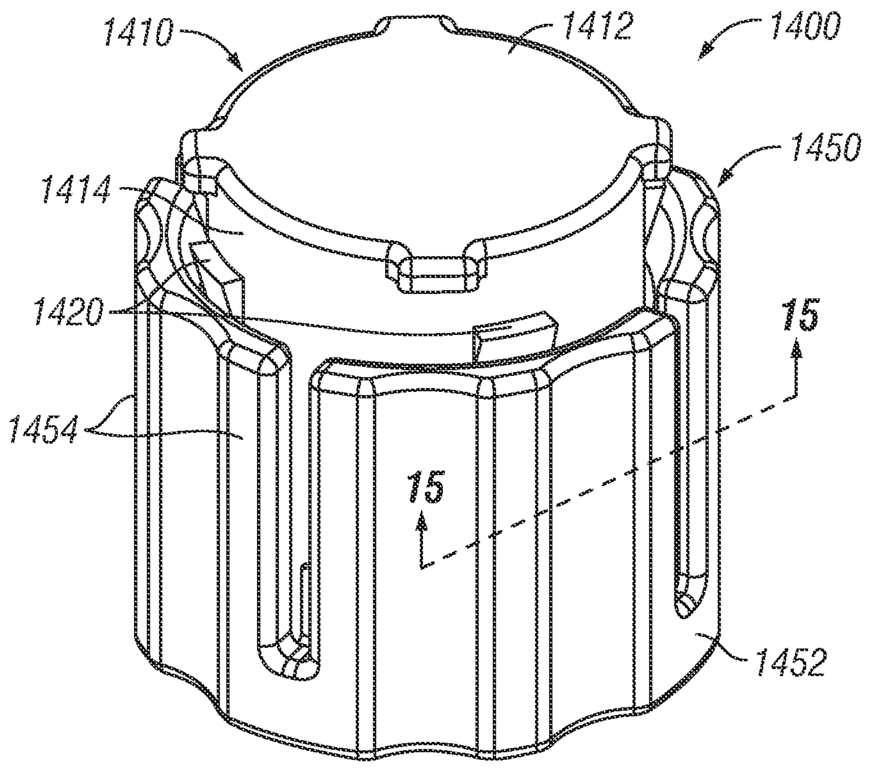
FIG. 14 is a perspective view of a safety cap in an unused configuration according to another illustrative embodiment.

FIG. 14 is a perspective view of another safety cap in in unused configuration according to an illustrative embodiment. The safety cap 1400 can be coupled to an NC, such as NC 100 in FIG. 1, to seal an opening at the distal end of the NC. In this embodiment in FIG. 14, the safety cap 1400 is generally cylindrical with an end wall 1412 at a first end which is separated from an opening 1416 at a second end by a side wall 1452. The opening 1416 at the second end of the safety cap 1400 leads into a cavity 1418, both of which are sized to receive a threaded head of a conventional NC.

In the illustrative embodiment in FIG. 14, the safety cap 1400 is formed from a first cap portion 1410, which may be referred to in the alternative as an inner cap 1410, and a second cap portion 1450, which may be referred to in the alternative as an outer cap 1450. The outer cap 1450 is a hollow cylinder open at its first end and second end, and partially encloses a volume of space occupied by the inner cap 1410. The inner cap 1410 has an end wall 1412 at a first end which transitions to a side wall 1414. The inner cap 1410 also has an opening 1416 at a second end that is opposite to the first end. The opening 1416 leads into a cavity 1418, which is shown in more detail in FIG. 18 that follows.

The inner cap 1410 and the outer cap 1450 are coaxially aligned and rotatably engaged with each other. In the unused configuration, the inner cap 1410 and the outer cap 1450 rotate together to only allow the safety cap 1400 to be attached to an NC. Thus, the inner cap 1410 and the outer cap 1450 rotate freely in the opposite direction to prevent unintended removal. For example, when the safety cap 1400 is being attached to an NC using a conventional luer lock interface, a rotational force in the clockwise direction causes the safety cap 1400 to be tightened onto the NC and a rotational force in the counterclockwise direction causes the outer cap 1450 to spin freely around the inner cap 1410, which prevents removal. In the used configuration depicted in FIG. 16, the outer cap 1450 and the inner cap 1410 rotate together to only allow the safety cap 1400 to be detached from the NC. Thus, the inner cap 1410 and the outer cap 1450 rotate freely in the opposite direction to prevent reattachment. For example, when the safety cap 1400 is being removed from the NC, the safety cap 1400 is transitioned from the unused configuration to the used configuration, a rotational force in the counterclockwise direction causes the safety cap 1400 to be loosened from the NC and a rotational force in the clockwise direction causes the outer cap 1450 to spin freely around the inner cap 1410 to prevent reattachment.

With reference to FIG. 14, in the unused configuration, the inner cap 1410 extends out of the second end of the outer cap 1450. Axial movement of the inner cap 1410 relative to the outer cap 1450 can be controlled by the axial locking wedges 1420 disposed around a circumference of the inner cap 1410. The axial locking wedges 1420 are configured to engage an axial locking flange 1456, shown in more detail in FIG. 15, disposed on an interior surface of the side wall 1452 of the outer cap 1450. Each of the axial locking wedges 1420 are wedge-shaped with the vertex pointing in the direction of the second end of the safety cap 1400 and the base facing the first end of the safety cap 1400. Operation of the axial locking wedges 1420 with the axial locking flange 1456 is described in more detail in the figures that follow.

The exterior surface of the side wall 1452 of the outer cap 1450 includes a plurality of elongated ridges 1454. The plurality of elongated ridges 1454 are grip-enhancing structures. Other forms of grip-enhancing structures can be substituted instead.

Figure 15:
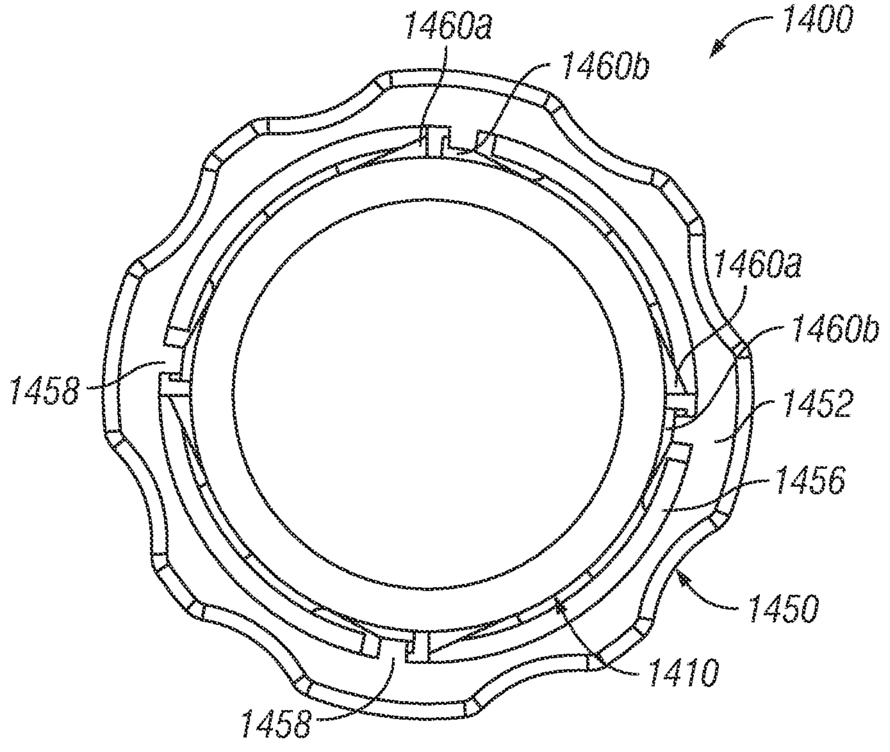
FIG. 15 is a cross-sectional view of the other safety cap according to an illustrative embodiment.

FIG. 15 is a cross-sectional view of the safety cap in FIG. 14, taken along line 15-15, according to an illustrative embodiment. The inner cap 1410 is housed within the volume of space defined by outer cap 1450. A cavity within the inner cap 1410, shown in more detail in FIG. 18, is sized to receive and engage a head of an NC. Although not shown, an engagement interface can be disposed on the interior surface of the side wall 1414 of inner cap 1410 for engaging the head of the NC. The engagement surface can be a threaded interface, such as a conventional luer lock interface.

The inner surface of the side wall 1452 of the outer cap 1450 includes an axial locking flange 1456 that projects radially inward towards an axis (not shown) common to both the inner cap 1410 and the outer cap 1450. The axial locking flange 1456 reduces an effective diameter of the outer cap 1450 and has a generally wedge-shaped cross-section that facilitates the set of axial locking wedges 1420 to cross over in only one direction, i.e., to permit axial movement of the inner cap 1410 relative to the outer cap 1450 in one direction to allow the safety cap 1400 can transition from the unused configuration to the used configuration, but which prevents axial movement of the outer cap 1450 relative to the inner cap 1410 in the other direction to transition back into the unused configuration from the used configuration. Operation of the axial locking wedges 1420 and the axial locking flange 1456 is described in more detail in FIG. 18.

In this non-limiting embodiment, the inner surface of the side wall 1452 of the outer cap 1450 includes a set of rotational stops 1458 that can be used in conjunction with a plurality of rotational locking wedges 1460 to control the direction of rotation of the inner cap 1410 relative to the outer cap 1450. The set of rotational stops 1458 project radially inward towards the shared axis and, based on the configuration of the safety cap 1400, i.e., in the unused configuration or the used configuration, either a first set of rotational locking wedges **1460*a* engages the set of rotational stops 1458 to permit one-directional, rotational movement of the outer cap 1450 relative to the inner cap 1410; or a second set of rotational locking wedges 1460*b* engages the set of rotational stops 1458 to permit the one-directional, rotational movement in the opposite direction of the outer cap 1450 relative to the inner cap 1410**.

For example, and with particular reference to the embodiment depicted in FIG. 15, if the inner cap 1410 is analogized as a cylinder having a base at the second end, the first set of rotational locking wedges **1460*a* are formed around a circumference of the inner cap 1410 at a first height relative to the base and each oriented similarly, i.e., with a vertex pointing in a first direction to engage each of the set of rotational stops 1458 when a counterclockwise force is applied to the outer cap 1450, and a base facing in a second direction to engage at least one of the set of rotational stops 1458 when a clockwise force is applied to the outer cap 1450. The second set of rotational locking wedges 1460*b* are formed around another circumference of the inner cap 1410 at a second height relative to the base which is different than the first height and each oriented similarly, but opposite to the orientation of the first set of rotational locking wedges 1460*a*, i.e., with a vertex pointing in the second direction to engage each of the set of rotational stops 1458 when a counterclockwise force is applied to the outer cap 1450, and a base facing in the first direction to engage at least one of the set of rotational stops 1458 when a clockwise force is applied to the outer cap 1450. Operation of the rotational locking wedges 1460 and the set of rotational stops 1458 are described in more detail in FIG. 17**.

Figure 16:
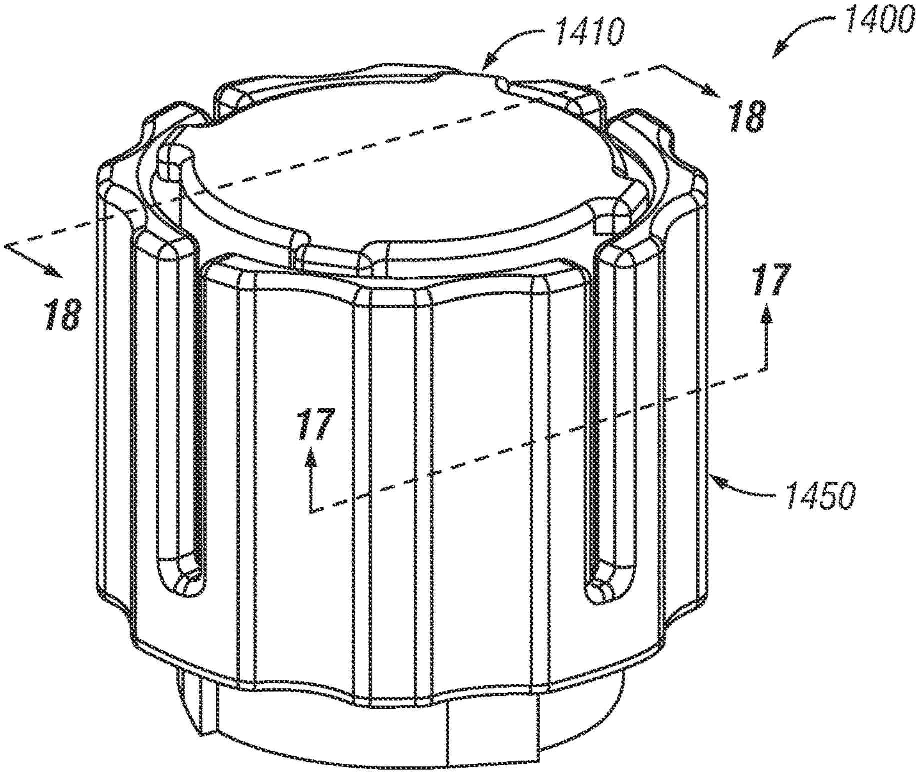
FIG. 16 is a perspective view of the other safety cap in a used configuration according to an illustrative embodiment.

FIG. 16 is a perspective view of the safety cap in FIG. 14 in a used configuration according to an illustrative embodiment. In the used configuration, the first end of the outer cap 1450 and the first end of the inner cap 1410 are substantially flush. At the second end of the safety cap 1400 the inner cap 1410 extends outwardly from the outer cap 1450. In this used configuration, the safety cap 1400 can be removed from an NC but cannot be reattached to any NC.

Figure 17:
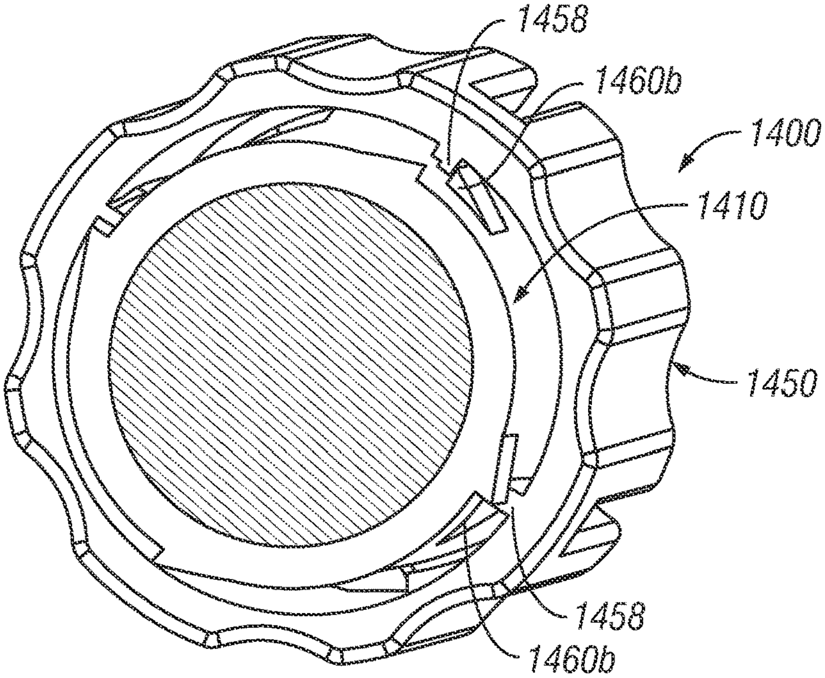
FIG. 17 is cross-sectional view of the other safety cap according to an illustrative embodiment.

FIG. 17 is cross-sectional view of the safety cap in FIG. 16 taken along line 17-17 according to an illustrative embodiment. The set of rotational stops 1458 are shown engaged with the set of rotational locking wedges **1460*b* that allows the safety cap 1400 to be removed from an NC, i.e., allows the inner cap 1410 and the outer cap 1450 to rotate together in the counterclockwise direction. When in the used configuration, a rotational force applied in the counterclockwise direction causes the face of each of the set of rotational locking wedges 1460*b* to engage the adjacent one of the set of rotational stops 1458, which causes the inner cap 1410 and the outer cap 1450 to rotate together in the counterclockwise direction. When in the used configuration, a rotational force applied in the clockwise direction causes each of the set of rotational stops 1458 to advance up and over the inclined surface of one of the set of rotational locking wedges 1460*b*. Thus, the rotational motion in the clockwise direction causes the outer cap 1450 to spin freely relative to the inner cap 1410**.

When the safety cap 1400 is in the unused configuration, as shown in FIGS. 14 and 15, the set of rotational stops 1458 are positioned to engage the set of rotational locking wedges **1460*a* that are oriented to allow the outer cap 1450 and the inner cap 1410 to rotate together in the clockwise direction to allow the safety cap 1400 to be tightened onto an NC. When in the unused configuration, a rotational force in the counterclockwise direction causes the outer cap 1450 to spin freely relative to the inner cap 1410. Operation of the safety cap 1400 in the unused configuration is analogous to the operation of the safety cap 1400** in the used configuration which is described in more detail in the preceding paragraph, but which is excluded herein for sake of brevity.

FIG. 18 is a cross sectional view of the safety cap in FIG. 16 taken along line 18-18 according to an illustrative embodiment. The safety cap 1400 is depicted in the used configuration with the first end of the inner cap 1410 substantially flush with the outer cap 1450. The second end of the inner cap 1410, which houses the opening 1416 leading into the cavity 1418, extends outwardly from the second end of the outer cap 1450. A set of axial locking wedges 1420 are shown with their vertices pointing in the direction of the second end of the safety cap 1400 and their bases facing the first end of the safety cap 1400. The bases of the set of axial locking wedges 1420 are engaged with the axial locking flange 1456 to prevent the inner cap 1410 from extending out of the first end of the outer cap 1450, i.e., preventing the safety cap 1400 from reattaining the unused configuration. As can be seen in this illustrative embodiment, the axial locking flange 1456 has a generally wedge-shaped cross-section that allows transition of the safety cap 1400 from the unused configuration to the used configuration, but which prevents the safety cap 1400 from transitioning from the used configuration back to the unused configuration.

FIG. 19A-19C are various perspective views of a safety cap with a use indicator according to an illustrative embodiment. The safety cap 1900 is formed from an outer cap 1950 and an inner cap 1910 housed within a cavity defined by the outer cap 1950. The application of a rotational force to the outer cap 1950 causes the outer cap 1950 to rotate relative to the inner cap 1910 to expose a use indicator 1912. In this illustrative embodiment, the use indicator 1912 is a color exposed during rotation of the outer cap 1950 relative to the inner cap 1910.

The exemplary safety cap 1900 shown in FIG. 19A can be secured to an NC 100 by imparting a rotational force to the safety cap 1900 in the direction of arrow 1902, i.e., twisting the safety cap 1900 in the clockwise direction when the safety cap 1900 is attached to the NC 100 using a conventional luer lock. Twisting the safety cap 1900 in an opposite direction of arrow 1902, i.e., in the counterclockwise direction, causes the outer cap 1950 to rotate relative to the inner cap 1910 to begin to expose the use indicators 1912 in the observation windows 1952, as shown in FIG. 19B. Once the use indicators 1912 are fully exposed, the outer cap 1950 and the inner cap 1910 are locked together, which allows the rotational force to be translated to the inner cap 1910 so that the safety cap 1900 can be unscrewed from the NC 100. Once unscrewed, the safety cap 1900 can be removed from the NC 100, as shown in FIG. 19C. Notably, when the use indicators 1912 are exposed in the observation windows 1952, notice is provided to medical care providers that the safety cap 1900 has already been used.

In this illustrative embodiment, the use indicators 1912 are exposed when the safety cap 1900 is unscrewed from the NC. However, in another embodiment, the use indicators 1912 can be exposed when the safety cap 1900 is screwed onto the NC. Thus, in this other embodiment the use indicators 1912 can be exposed by a rotational force applied in the direction of arrow 1902. In either embodiment, once the use indicators 1912 are exposed, the outer cap 1950 and the inner cap 1910 can be locked together to prevent inadvertent further rotational movement that could result in concealment of the use indicators 1912.

Figure 20A:
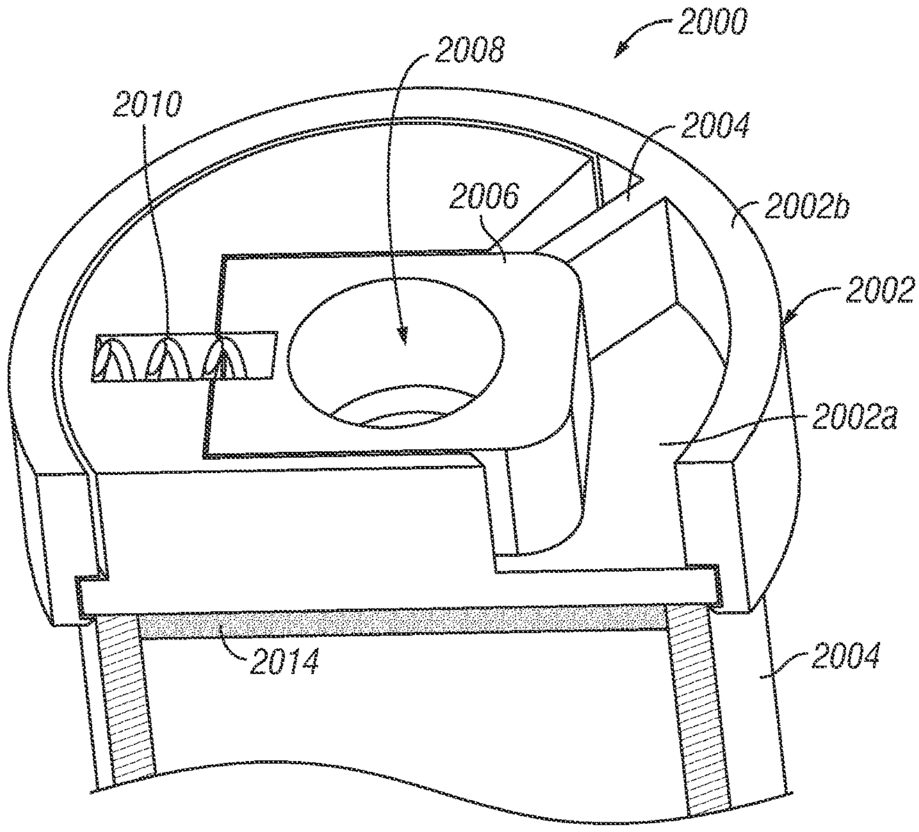
FIG. 20A is a perspective, cross-sectional view of a safety cap in an unused configuration according to another illustrative embodiment.

FIG. 20A is a perspective, cross-sectional view of a safety cap in an unused configuration according to another illustrative embodiment. Generally, the safety cap 2000 includes a body formed from a lid 2002 connected to a collar 2004. In some embodiments, the lid 2002 and the collar 2004 are integrally formed and in other embodiments the lid 2002 and the collar 2004 are fixedly secured together. The collar 2004, which may also be referred to in the alternative as a fastener, couples the safety cap 2000 to an NC, such as NC 100 in FIG. 1. The collar 2004 can couple the safety cap 2000 to the NC using any number of conventional fastening technologies, such as adhesives, friction fit interfaces, or other known mechanical fasteners, such as a threaded interface. In this example in FIG. 20A, the collar 2004 is configured to be rotatably engaged with an NC such as through a threaded interface via threads (not shown) disposed on an interior surface of the collar.

In the exemplary embodiment depicted in FIG. 20, the lid 2002 includes a base 2002*a* that is fixed relative to the collar 2004, and a rotating sidewall 2002*b* that can rotate around the base 2002*a*. Attached to the rotating sidewall 2002*b* is a retaining pin 2004 that projects radially inward and is engaged with a sliding gate 2006 when the safety cap 2000 is in the opened configuration. When the safety cap 2000 is in the opened configuration and fully engaged with an NC, such as NC 100 in FIG. 1, the head at the distal end of the NC is aligned with the gate opening 2008 defined by the sliding gate 2006 so that a fluid transfer device is insertable through the gate opening 2008 to engage the distal end of the NC. The sliding gate 2006 is under a compressive force by a spring 2012, which is opposed by the retaining pin 2004 so that the sliding gate 2006 can be maintained in the opened configuration.

Figure 20B:
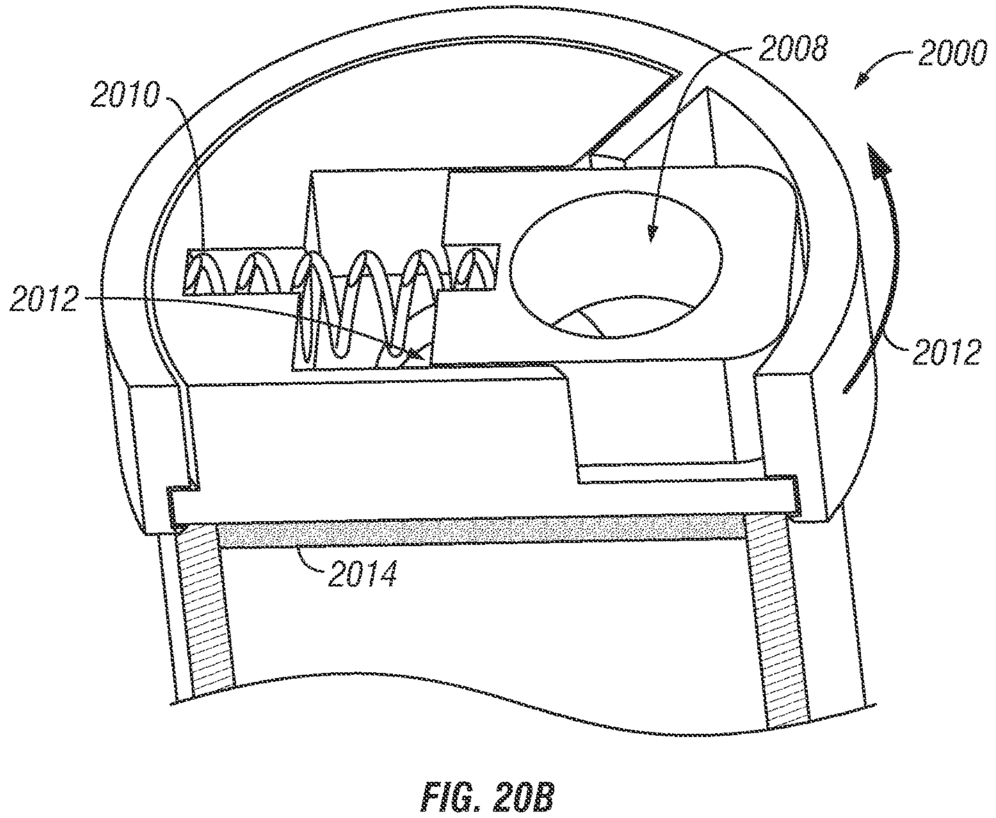
FIG. 20B is a perspective, partial cross sectional view of a safety cap in a used configuration according to an illustrative embodiment.

FIG. 20B is a perspective, partial cross sectional view of a safety cap in a used configuration according to an illustrative embodiment. In a non-limiting embodiment, the closed configuration of safety cap 2000 can be achieved by removing the safety cap 2000 from an NC, e.g., by unscrewing the safety cap 2000 from the NC with application of a force on the rotating sidewall 2002*b* in counterclockwise direction as indicated by the arrow 2012. Rotation of the rotating sidewall 2002*b* causes the retaining pin 2004 to disengage from the sliding gate 2006, allowing the spring 2012 to eject the sliding gate 2006 from its original docked location. When the sliding gate 2006 is ejected, the gate opening 2008 in the sliding gate 2006 is misaligned from the base opening 2012 in the base 2002*a*, which is always aligned with the opening in the head of the NC. The misalignment of openings 2008 and 2012 prevents a syringe or other type of fluid transfer device from being engaged with an NC, which can prevent the safety cap 2000 from being inadvertently reused. Thus, the slidable gate 2006 in FIG. 20 can serve as a use indicator that can indicate to a user that the safety cap 2000 has been previously attached to an NC, i.e., that the safety cap 2000 has been used.

With particular reference to safety cap 2000, the spring-activated sliding gate 2006 and the retaining pin 2004 form a detent that prevents the safety cap 2000 from transitioning from the used configuration in FIG. 20B back into the unused configuration in FIG. 20A. The detent is triggered when a decoupling force is applied to the safety cap 2000 to remove the safety cap 2000 from an NC.

Safety cap 2000 can include a disinfectant applicator 2014 housed within the lid 2002. The disinfectant applicator 2014 can be a sponge-like material soaked with enough disinfectant to provide disinfectant capabilities for at least a week. The disinfectant applicator 2014 can be engaged by the distal end of an NC, such as the distal end of NC 100 in FIG. 1, as the safety cap 2000 is being attached to the NC. In one embodiment, when the safety cap 2000 is fully engaged with the NC, the distal end of the NC breaks through the disinfectant applicator 2014, providing tactile and/or auditory feedback that the safety cap 2000 is fully engaged with the NC. In some embodiments, the disinfectant applicator 2014 can have perforations (not shown) at an area that coincides with the base opening 2012 in the base 2002*a* of the lid 2002 to facilitate penetration by the NC.

Figure 21A:
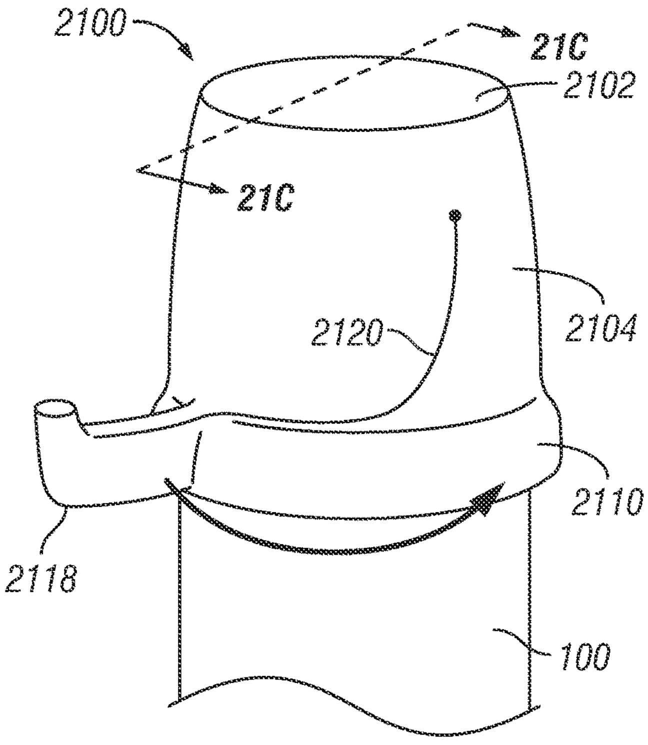
FIGS. 21A-D are views of a peelable safety cap according to an illustrative embodiment.
Figure 21B:
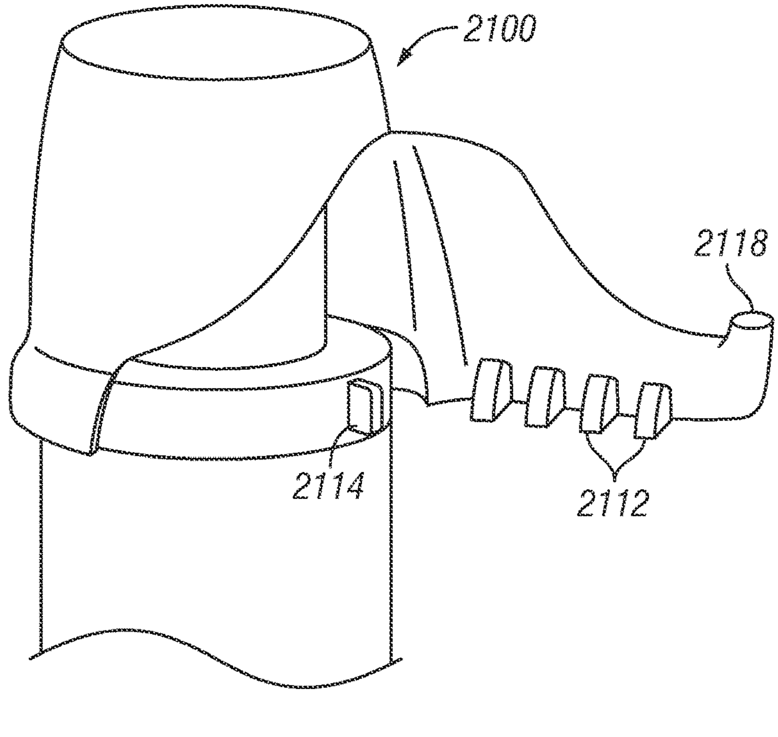
Figure 21C:
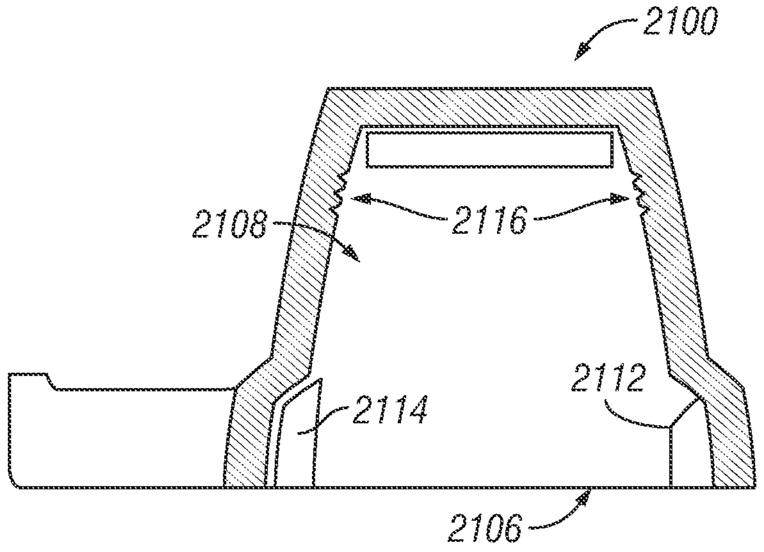
Figure 21D:
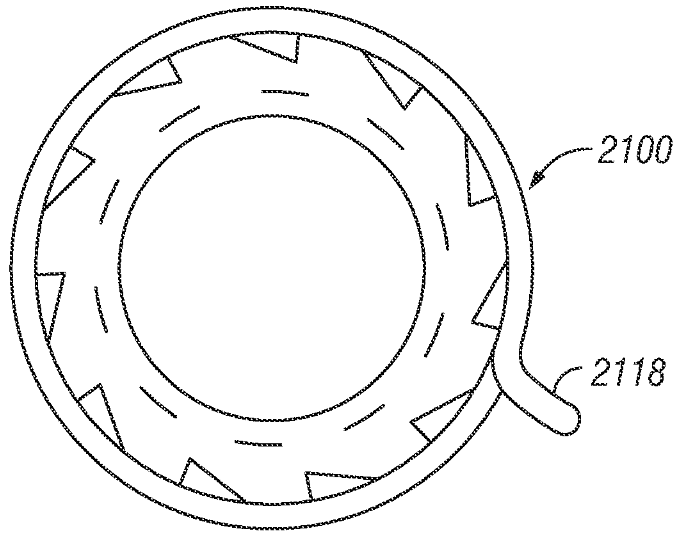

FIGS. 21A-D are views of a peelable safety cap according to an illustrative embodiment. In particular, FIG. 21A is a perspective view of a peelable safety cap 2100 in a closed configuration and FIG. 21B is a perspective view of the peelable safety cap 2100 in a partially opened configuration. FIG. 21C is a cross-sectional view of the safety cap 2100 taken along line 21C-21C in FIG. 21A, and FIG. 21D is a view of the cavity 2108 inside the safety cap 2100, looking in from the flared base 2110.

The safety cap 2100 is generally cylindrical in shape with an end wall 2102 at a first end which transitions into a side wall 2104. The safety cap 2100 has an opening 2106 at a second end that is opposite to the first end. The opening 2106 leads into a cavity 2108 sized to receive the head of an NC 100. A base 2110 of the safety cap 2100 is flared to accommodate a plurality of rotational locking wedges 2112, which are configured to restrict the rotational motion of the safety cap 2100 when attached to the NC 100. Rotational motion of the safety cap 2100 is restricted by engagement of the plurality of rotational locking wedges 2112 with the rotational stopper 2114 projecting radially outwardly from the body of the NC 100, as described in more detail in the paragraphs that follow.

The exemplary safety cap 2100 in FIG. 21A is shown attached to NC 100 with a head at the distal end of the NC enclosed within the cavity 2108. The safety cap 2100 is configured to be attached to the NC 100 using conventional fasteners but which can only be removed from the NC 100 when in the safety cap 2100 is torn open to achieve the partially opened configuration shown in FIG. 21B. In this illustrative embodiment, the safety cap 2100 is configured to be attached to the NC 100 using a luer lock interface 2116 disposed on an interior surface of the side wall 2104, as can be seen in the cross-sectional view of the safety cap 2100 in FIG. 21C.

Each of the plurality of rotational locking wedges 2112 is shaped to permit the safety cap 2100 to rotationally engage with the NC 100 in the clockwise direction so that the safety cap 2100 can be tightened onto the NC 100. With particular reference to FIG. 21D, each of the rotational locking wedges 2112 are oriented similarly, i.e., with a vertex pointing in a first direction to engage the rotational stopper 2114 when a rotational force is applied to the safety cap 2100 in the clockwise direction, and with a base facing in a second direction to engage the rotational stopper 2114 when the rotational force is applied to the safety cap 2100 in the counterclockwise direction. Thus, the rotational force applied to the safety cap 2100 in the clockwise direction to secure the safety cap 2100 to the NC 100 causes the rotational stopper 2114 of the NC 100 to advance up and over each of the rotational locking wedges 2112, which allows the safety cap 2100 to be tightened onto the NC 100. A rotational force in the counterclockwise direction causes the base of one or more of the rotational locking wedges 2112 to engage the rotational stopper 2114, which prevents rotation in the counterclockwise direction. In some embodiments, the rotational stopper 2114 is integrally formed with the NC. When the grasping tab 2118 is peeled away from the safety cap 2100, one or more of the rotational locking wedges 2112 adjacent to the rotational stopper 2114 are extracted from the rotational path of the rotational stopper 2114, which allows the safety cap 2100 to rotate sufficiently in the counterclockwise direction to permit removal. In some embodiments, the grasping tab 2118 transitions to a separations interface 2120.

With particular reference to safety cap 2100, the rotational locking wedges 2112 and the rotational stopper 2114 form a detent system that prevents the safety cap 2100 from being unscrewed from the head of the NC. Removal of the safety cap 2100 is achieved by destroying the body of the safety cap 2100 by pulling on the grasping tab 2118 as previously described.

Figure 22A:
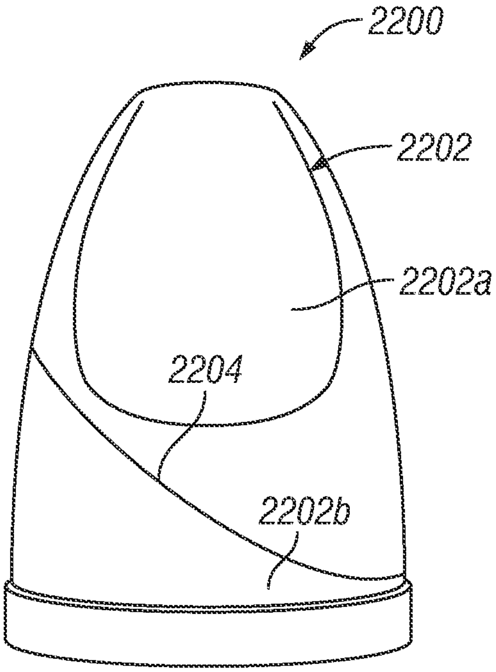
FIGS. 22A-C are views of another peelable safety cap according to an illustrative embodiment.
Figure 22B:
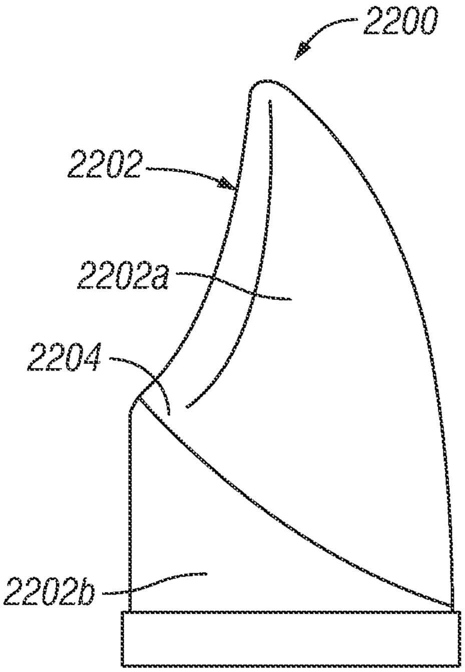
Figure 22C:
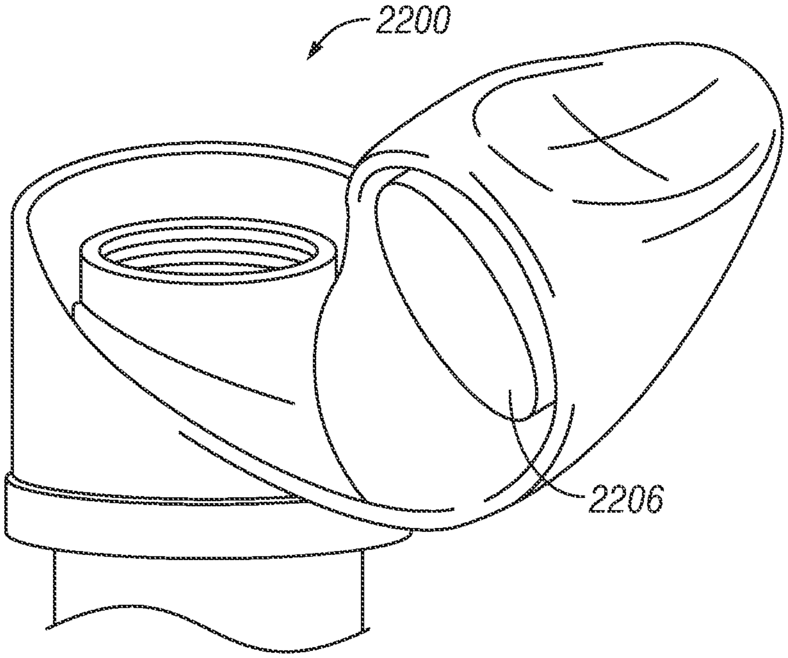

FIGS. 22A-C are various views of another peelable safety cap in an unused configuration according to an illustrative embodiment. Specifically, FIGS. 22A and 22B are views of safety cap 2200 in an unused configuration, and FIG. 22C is a view of the safety cap 2200 in a used configuration.

The safety cap 2200 is formed generally from an outer cover 2202 that houses an attachment interface (not shown) housed within a cavity of the outer cover 2202. The attachment interface can be a threaded interface that allows the safety cap 2200 to be attached to conventional NCs configured with a luer lock interface, such as NC 100 in FIG. 1. When the safety cap 2200 is attached to the NC, at least the head located at the distal end of the NC is housed within the cavity to protect the opening from inadvertent contamination.

In the exemplary safety cap 2200 depicted in FIGS. 22A-C, the outer cover 2202 is formed from an endcap 2202*a* and a base 2202*b*. Once attached to the NC, the opening at the distal end of the NC can be exposed by tearing away the end cap 2202*a* from the base 2202*b* along the score line 2204 to achieve the used configuration depicted in FIG. 22C. The score line 2204 extends at least partially around the circumference of the safety cap 2200. In this illustrative embodiment, the score line 2204 extends only partially around the safety cap 2200 so that the endcap 2202*a* remains attached to the base 2202*b*. The dangling endcap 2202*a* can serve as a visual indicator that the safety cap 2200 has already been used and also obviates the inconvenience of separate disposal of the endcap 2202*a* during use.

In one embodiment, the outer cover 2202 of the safety cap 2200 is formed from a flexible material, such as latex or plastic. In some embodiments, a cleaning surface 2206 is housed within the endcap 2202*a* and configured to engage a head at the distal end of an NC when the safety cap 2200 is in the closed configuration. The cleaning surface 2206 can be saturated with a disinfectant that is applied to a distal end of the NC when the safety cap 2200 is coupled with the NC and in the closed configuration. In another embodiment, the cleaning surface 2206 can be in fluid contact with a reservoir (not shown) housed within the endcap 2202*a* and configured to release disinfectant when the endcap 2202*a* is squeezed. In this embodiment, removal of the endcap 2202*a* to expose the head at the distal end of the NC provides the squeezing force that applies disinfectant to the distal end of the NC before the NC is exposed.

Figure 23A:
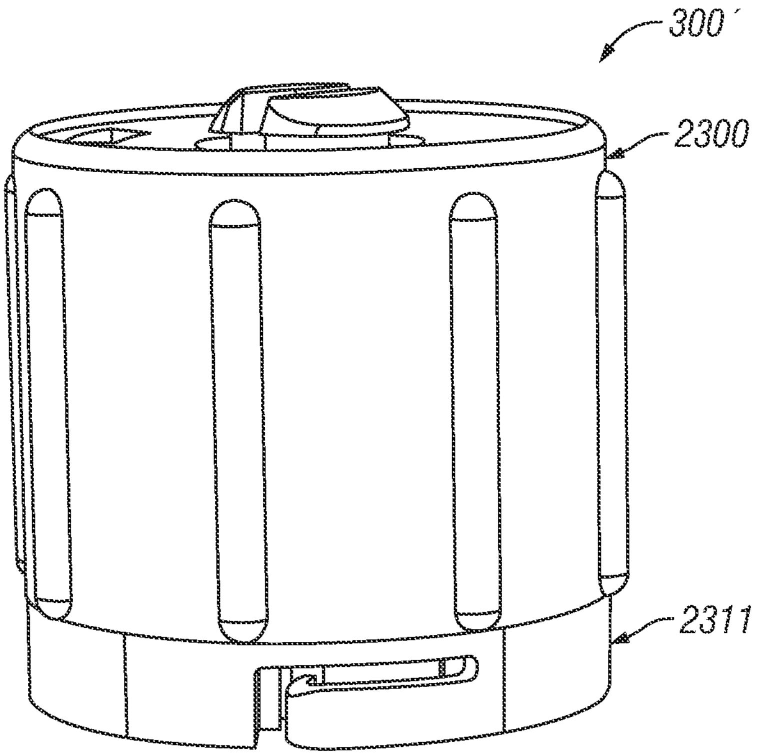
FIGS. 23A-C are schematic diagrams showing alternate perspective views of a single use safety cap according to an illustrative embodiment.
Figure 23B:
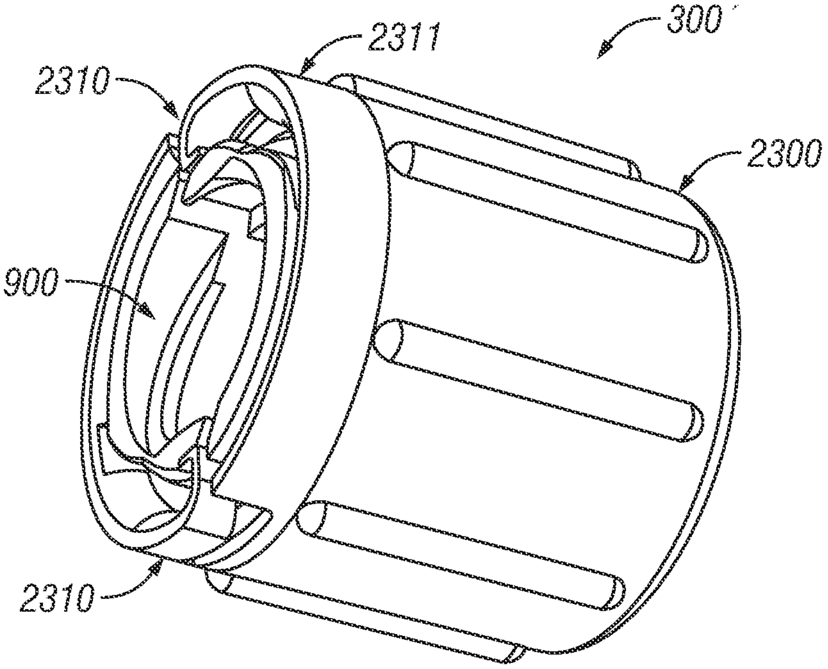
Figure 23C:
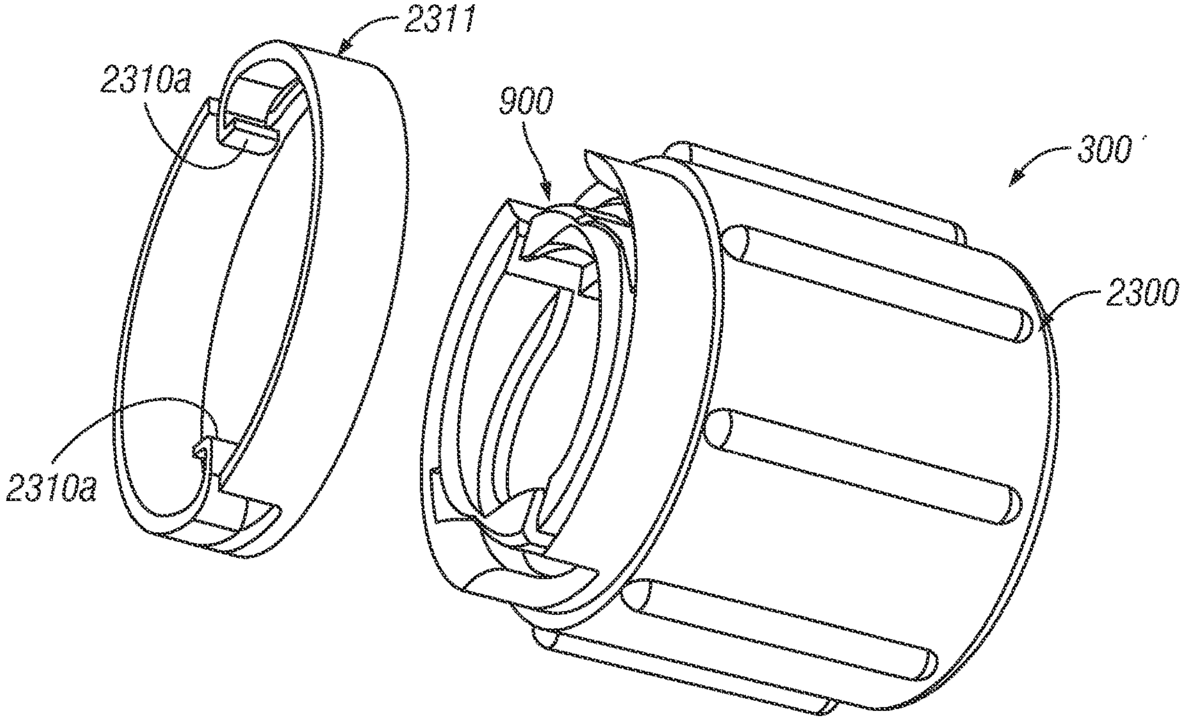

FIGS. 23A, 23B, and 23C are schematic diagrams showing alternate perspective views of a single use safety cap according to an illustrative embodiment. The safety cap 300' depicted in FIGS. 23A-23C is similar to the safety cap 300 in FIG. 3, but with a modified outer cap 2300. In particular, outer cap 2300 differs from outer cap 700 in the set of thread deformers 2310 are disposed on an annulus 2311. The pressing surfaces 2310*a* project radially inward from the annulus 2311 and can engage with deformable thread portions 920 of the inner cap 900, which can prevent reattachment of the safety cap 300' as described previously.

Figure 24:
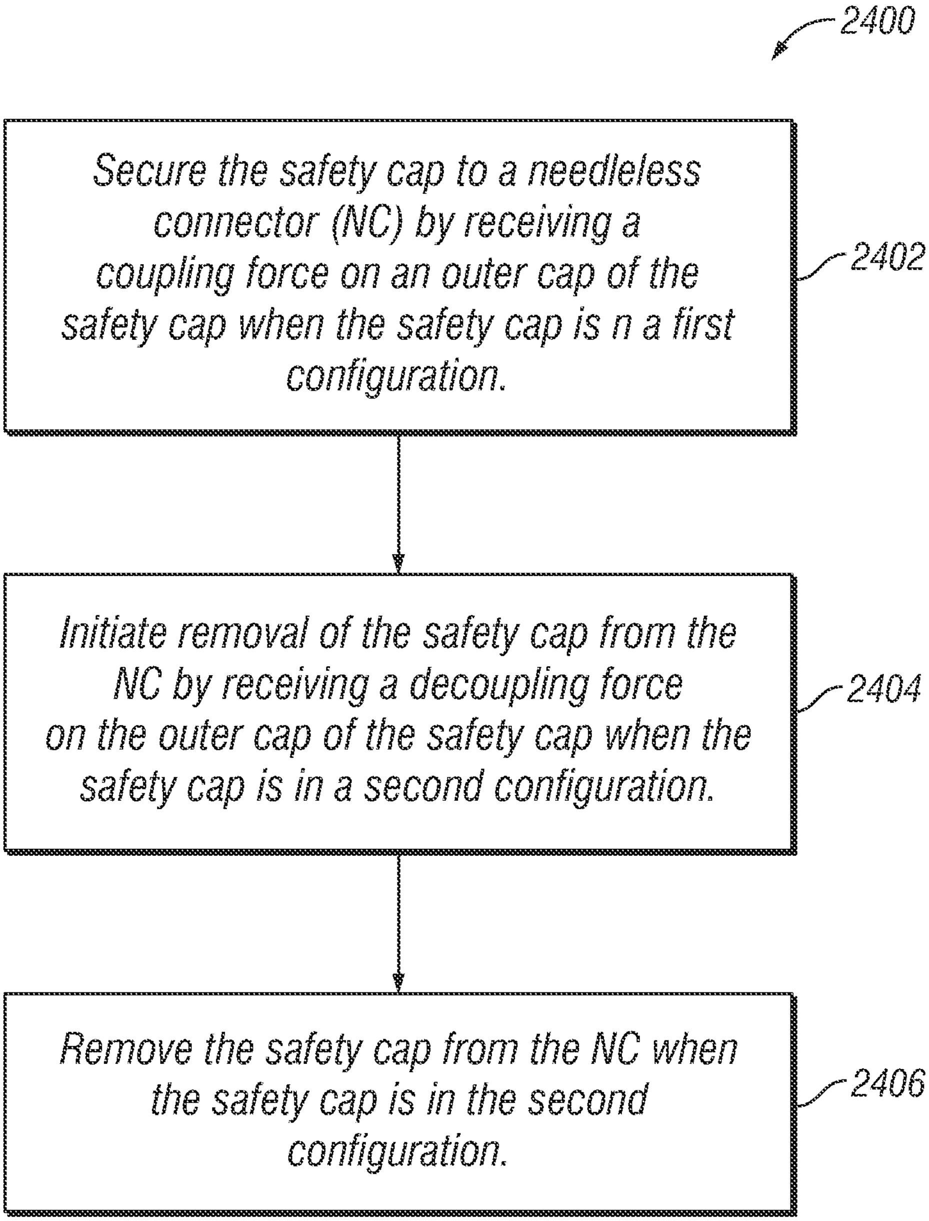
FIG. 24 is a flowchart of a process for operating a safety cap in accordance with an illustrative embodiment.

FIG. 24 is a flowchart of a process for operating a safety cap in accordance with an illustrative embodiment. The steps of flowchart 2400 can be carried out by a safety cap, such as safety caps 300 and 1400 in FIGS. 3 and 14, respectively.

In step 2402, a coupling force is received on an outer cap of the safety cap when the safety cap is in a first configuration. The coupling force is provided to secure the safety cap onto the NC. In some embodiments, the coupling force is a rotational force in a first direction, e.g., clockwise direction.

In step 2404, a decoupling force is received on the outer cap of the safety cap when the safety cap is in a second configuration. The decoupling force is provided to remove the safety cap from the NC. In some embodiments, the decoupling force is a rotational force in an opposite direction of the first rotational force, e.g., in a counterclockwise direction. In some other embodiments, the decoupling force is a tearing force applied to a grasping tab to tear the body of a safety cap, as in the embodiment described in FIG. 21.

In step 2406, the safety cap is removed from the NC when the safety cap is in the second configuration. In one embodiment, the safety cap is removed by a force applied in an axial direction.

Although embodiments of the invention have been described with reference to several elements, any element described in the embodiments described herein are exemplary and can be omitted, substituted, added, combined, or rearranged as applicable to form new embodiments. A skilled person, upon reading the present specification, would recognize that such additional embodiments are effectively disclosed herein. For example, where this disclosure describes characteristics, structure, size, shape, arrangement, or composition for an element or process for making or using an element or combination of elements, the characteristics, structure, size, shape, arrangement, or composition can also be incorporated into any other element or combination of elements, or process for making or using an element or combination of elements described herein to provide additional embodiments.

Additionally, where an embodiment is described herein as comprising some element or group of elements, additional embodiments can consist essentially of or consist of the element or group of elements. Also, although the open-ended term "comprises" is generally used herein, additional embodiments can be formed by substituting the terms "consisting essentially of" or "consisting of."

While this invention has been particularly shown and described with reference to preferred embodiments, it will be understood by those skilled in the art that various changes in form and detail may be made therein without departing from the spirit and scope of the invention. For example, certain components of the various safety caps described herein are shown to have wedge-shapes (either in overall form or in cross-section); however, in other embodiments, other shapes can be substituted provided that relative motion of the safety cap components can still be controlled. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A safety cap for needleless connectors, the cap comprising:

a body configured to at least partially enclose a head of the needleless connector (NC), wherein:

the body includes a first cap portion housed within a second cap portion, the body is configured to achieve a first configuration that can be securely sealed to the NC and a second configuration that cannot be securely sealed to the NC, and the second configuration is different from the first configuration; and a detent in communication with the body, wherein:

the detent includes a set of deformable thread portions engaged with the first cap portion and a set of thread deformers engaged with the second cap portion, and engagement of the set of deformable thread portions with the set of thread deformers prevents the body from transitioning from the second configuration back to the first configuration.

2. The safety cap of claim 1, wherein first cap portion includes an end wall connected to a side wall that defines a cylindrical cavity sized to receive a head disposed at a distal end of the NC.

3. The safety cap of claim 2, wherein the second cap portion includes an end wall connected to a side wall that defines a cylindrical cavity sized to receive the first cap portion, and wherein:

the end wall of the second cap portion defines an aperture coinciding with an axis common to the first cap portion and the second cap portion, the detent includes a locking post projecting normally from the end wall of the first cap portion and aligned coaxially with the common axis, the locking post includes a frusto-conical cap at its terminal end, the locking post extends at least partially through the aperture so that the frusto-conical cap transitions from within the cavity to outside of the cavity when the safety cap transitions from the first configuration to the second configuration.

4. The safety cap of claim 3, wherein the set of thread deformers projects radially inwardly into the cavity, wherein the first cap portion includes a set of guidance channels disposed on an outer surface of the first cap portion, and wherein:

the set of guidance channels includes a first set of guidance channels that terminates at the set of deformable thread portions; and the first set of guidance channels is sized to receive the set of thread deformers to guide the set of thread deformers to the set of deformable thread portions as the safety cap transitions from the first configuration to the second configuration.

5. The safety cap of claim 4, wherein an interior surface of the cylindrical cavity further comprises a threaded interface, wherein engagement of the set of thread deformers with the set of deformable thread portions changes a thread pitch at the leading edge of the threaded interface, and wherein the changed thread pitch prevents the safety cap from reattaching to another NC.

6. The safety cap of claim 4, wherein an interior surface of the cylindrical cavity further comprises a threaded interface, wherein engagement of the set of thread deformers with the set of deformable thread portions reduces an effective diameter of the opening of the cylindrical cavity, and wherein the reduction of the effective diameter prevents the safety cap from reattaching to another NC.

7. The safety cap of claim 4, wherein the second cap portion further comprises a set of track followers that project radially inwardly into the cavity, wherein the set of guidance channels further comprises a second set of guidance channels sized to receive the set of track followers, and wherein:

the second set of guidance channels terminates at receiving groove; and the second set of guidance channels is configured to guide the set of track followers to the receiving groove as the safety cap transitions from the first configuration to the second configuration.

8. The safety cap of claim 7, wherein reception of the set of guidance channels into the receiving groove locks the second cap portion and the first cap portion together to transfer a rotational force exerted on the second cap portion to the first cap portion.

* * * * *